United States Patent
D'Espaux et al.

(10) Patent No.: US 11,365,431 B2
(45) Date of Patent: *Jun. 21, 2022

(54) YEAST CELLS AND METHODS FOR PRODUCING FATTY ALCOHOLS

(71) Applicant: The Regents of the University of California, Oakland, CA (US)

(72) Inventors: Leopold D'Espaux, San Francisco, CA (US); Jay D. Keasling, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/786,558

(22) Filed: Feb. 10, 2020

(65) Prior Publication Data

US 2020/0231990 A1   Jul. 23, 2020

Related U.S. Application Data

(63) Continuation of application No. 15/979,144, filed on May 14, 2018, now Pat. No. 10,557,152.

(60) Provisional application No. 62/505,725, filed on May 12, 2017.

(51) Int. Cl.
| | |
|---|---|
| C12P 7/04 | (2006.01) |
| C12N 9/02 | (2006.01) |
| C12N 9/10 | (2006.01) |
| C12N 9/00 | (2006.01) |
| C12N 15/52 | (2006.01) |

(52) U.S. Cl.
CPC .............. *C12P 7/04* (2013.01); *C12N 9/0008* (2013.01); *C12N 9/1029* (2013.01); *C12N 9/93* (2013.01); *C12N 15/52* (2013.01); *C12Y 101/01001* (2013.01); *C12Y 102/01084* (2015.07); *C12Y 203/0102* (2013.01); *C12Y 203/01085* (2013.01); *C12Y 604/01002* (2013.01)

(58) Field of Classification Search
CPC ...... C12N 9/1029; C12N 9/0008; C12N 9/93; C12N 15/52; C12Y 102/01084; C12Y 203/0102; C12Y 604/01002; C12Y 101/01001; C12Y 203/01085; C12P 7/04
See application file for complete search history.

(56) References Cited

U.S. PATENT DOCUMENTS

| 10,557,152 B2 * | 2/2020 | D'Espaux ...... C12Y 203/01085 |
| 2016/0215308 A1 | 7/2016 | Weerawat |
| 2016/0237444 A1 | 8/2016 | Neilsen |
| 2016/0304913 A1 | 10/2016 | Gatter |

FOREIGN PATENT DOCUMENTS

WO   2016159869   10/2016

OTHER PUBLICATIONS

D'Espaux et al., Engineering high-level production of fatty alcohols by *Saccharomyces cerevisiae* from lignocellulosic feedstocks. Metabolic Engineering, 2017, vol. 42: 115-125. (Year: 2017).*
Broun et al., Catalytic plasticity of fatty acid modification enzymes underlying chemical diversity of plant lipids. Science, 1998, vol. 282: 1315-1317. (Year: 1998).
Devos, et al., Practical limits of function prediction. Proteins: Structure, Function, and Genetics. 2000, vol. 41 98-107 (Year: 2000).
Seffernick, et al., Melamine deaminase and Atrazine chlorohydrolase: 98 percent identical but functionally different. J. Bacteriol., 2001, vol. 83 (8): 2405-2410. (Year: 2001).
Whisstock, et al., Prediction of protein function from protein sequence. Q. Rev. Biophysics., 2003, vol. 36 (3): 307-340 (Year: 2003).
Witkowski, et al., Conversion of b-ketoacyl synthase to a Malonyl Decarboxylase by replacement of the active cysteine with Glutamine. Biochemistry, 1999. vol. 38: 11643-11650 (Year: 1999).
Batth, et al., "Targeted Proteomics for Metabolic Pathway Optimization, in: Fungal Secondary Metabolism: Methods and Protocls," Methods in Molecular Biology, vol. 944, pp. 47-58 (2012). doi: 10.1007/978-1-62703-122-6.
Brachmann, et al., "Designer deletion strains derived from *Saccharomyces cerevisiae* S288C: A useful set of strains and plasmids for PCR-mediated gene disruption and other applications." Yeast. vol. 14, pp. 115-132 (1998). doi10.1002/(SICI)1097-006(Jan. 30, 1998)14:2<115::AID-YEA204?3.0.CO;2-2.
Caspeta, et al., "Economic and environmental impacts of microbial biodiesel." Nat. Biotechnol. vol. 31, pp. 789-793 (2013). doi:10.1038/nbt.2683.
Clomburg, et al., "Integrated engineering of β-oxidation reversal and ω-oxidation pathways for the synthesis of medium chain ω-functionalized carboxylic acids." Metab. Eng. vol. 28, pp. 202-212 (2015). doi: 10.1016/j.ymben.2015.01.007.
Connor et al., "The United Nations World Water Development Report." Educational, Scientific, and Cultural Organization. Waer and Jobs. Paris France UNESCO (2016). ISBN 978-92-3-100146-8.
Degreif, et al., "Lipid engineering reveals regulatory roles for membrane fluidity in yeast flocculation and oxygen-limited growth." Metab. Eng. vol. 41, pp. 46-56 (2017). doi:10.1016/j.ymben.2017.03.002.

(Continued)

*Primary Examiner* — Ganapathirama Raghu
(74) *Attorney, Agent, or Firm* — Robin C. Chiang; Lawrence Berkeley National Laboratory

(57) ABSTRACT

The present invention provides for a genetically modified yeast cell comprising at least six or more of the following modifications: increased expression of *Mus musculus* fatty acid reductase, acetyl-CoA carboxylase, fatty acid synthase 1, fatty acid synthase 2, a mutant of the bottleneck enzyme encoded by ACC1 insensitive to post-transcriptional and post-translational repression, and/or a desaturase encoded by OLE1, and reduced expression of DGA1, HFD1, ADH6, and/or GDH1. The present invention provides a method for constructing the genetically modified yeast cell, and a method for producing a fatty alcohol from the genetically modified yeast cell.

26 Claims, 8 Drawing Sheets

Specification includes a Sequence Listing.

(56) References Cited

OTHER PUBLICATIONS

Feng, et al., "Metabolic engineering of *Saccharomyces cerevisiae* to improve 1-hexadecanol production." Metab. Eng. vol. 27, pp. 10-19 (2015). doi:10.1016/j.ymben.2017.03.002.

Gaikwad, et al., "Fatty Alcohol Market Size," Industry Analysis Report: Forecast—2023 (2015) Ocean View, DE.

Garcia-Martin, et al., "A Method to Constrain Genome-Scale Models with 13C Labeling Data." PLOS Computational Biology. Research Article. vol. 11 (2015). e1004363. doi:10.1371/journal.pcbi.1004363.

Ghosh, et al., "(13)C Metabolic Flux Analysis for Systematic Metabolic Engineering of *S. cerevisiae* for Overproduction of Fatty Acids." Frontiers in BioEngineering and BioTechnology. vol. 4, p. 76 (2016). doi:10.3389/fbioe.2016.00076.

Gietz, et al., transformation of yeast by lithium acetate/single-stranded carrier DNA/polyethylene glycol method. Methods Enzymol. 350, 87-96 (2002).

Goh, et al., "Engineering of bacterial methyl ketone synthesis for biofuels." Applied and Environmental Microbiology. vol. 78, pp. 70-80 (2012). doi: 10.1128/AEM. 06785-11.

Guo, et al., "Minimization of glycerol synthesis in industrial ethanol yeast without influencing its fermentation performance." Metabolic Engineering. vol. 13, pp. 49-59 (2011). doi:10.1016/j.ymben.2010.11.003.

Haushalter, et al., "Production of anteiso-branched fatty acids in *Escherichia coli*; next generation biofuels with improved cold-flow properties." Metabolic Engineering. vol. 26C, pp. 111-118 (2014). doi:10.1016/j.ben.2014.09.002.

Hoja, et al., "HFA1 encoding an organelle-specific acetyl-CoA carboxylase controls mitochondrial fatty acid synthesis in *Saccharomyces cerevisiae*." The Journal of Biological Chemistry. vol. 279, pp. 21779-86 (2004). doi:10.1074/jbc.M401071200.

Kalscheuer, et al., "Microdiesel: *Escherichia coli* engineered for fuel production." Microbiology vol. 152, pp. 2529-2536. (2006) doi:10.1099/mic.0.29028-0.

Kildegaard, et al., "Engineering and systems-level analysis of *Saccharomyces cerevisiae* for production of 3-hydroxypropionic acid via malonyl-CoA reductase-dependent pathway." Microbial Cell Factories. vol. 15, p. 13 (2016). doi: 10.1186/s12934-016-0451-5.

Lee, et al., A Highly-characterized Yeast Toolkit for Modular, Multi-part Assembly. ACS Synthetic Biology. Research Article, 12 pgs (2015). 150414151809002. doi:10.1021/sb500366v.

Liu, et al., "Fatty alcohol production in engineered *E. coli* expressing Marinobacter fatty acyl-CoA reductases." Applied Microbiol Biotechnology. BioEnergy and BioFuels. vol. 97, pp. 7061-7071 (2013). doi:10.1007/s00253-013-5027-2.

Mazzoleni, et al., "A novel process-based model of microbial growth: self-inhibition in *Saccharomyces cereevisiae* aerobic fed-batch cultures." Microbial Cell Factories. vol. 14, p. 109 (2015). doi:10.1186/s1294-015-0295-4.

Mo, et al., "Connecting extracellular metabolomic measurements to intracellular flux states in yeast." Bio Med Central, BMC Systems Biology. vol. 3, p. 37 (2009). doi:10 1186/1752-0509-3-37.

Montague, et al., "CHOPCHOP: A CRISPR/Cas9 and TALEN web tool for genome editing." Nucleic Acids Res. 42. 401-407 (2014). doi:10.1093/nar/gku410.

Natter, et al., The spatial organization of lipid synthesis in the yeast *Saccharomyces cerevisiae* derived from large scale green fluorescent protein tagging and high resolution microscopy. Mol. Cell. Proteomics. vol. 4, pp. 662-672 (2005). doi:10/1074/mcp.M400123-MCP200.

Petkovic, et al., "Novel biocompatible cholinium-based ionic liquids—toxicity and biodegradability." Green Chem. 12, 643 (2010). doi:10.1039/b922247b.

Pfleger, et al, "Metabolic engineering strategies for microbial synthesis of oleochemicals." Metab. Eng. vol. 29, pp. 1-11 (2015). doi:10.1016/j.ymben.2015.01.009.

Qiao, et al., "Engineering lipid overproductionin the oleaginous yeast Yarrowia lipolytica." Metab. Eng. vol. 29, pp. 56-65 (2015). doi:10.1016/j.ymben.2015.02.005.

Reider-Apel, et al., "ACas9-based toolkit to program gene expression in *Saccharomyces cerevisiae*." Nucleic Acids Res. pp. 1-14 (2016). doi:10.1093/gbe/evw245.

Rungupham, et al., "Metabolic Engineering of *Saccharomyces cerevisiae* for Production of Fatty Acid-Derived Biofuels and Chemicals." Metab. Eng. vol. 21, pp. 103-113 (2013). doi:10.1016/j.ymben.2013.07.003.

Shi, et al., "Improving Production of Maloynl Coenzyme A-Derived Metabolites." Research Article. mbio.asm.org MBio, vol. 5, No. 3, pp. 1130-14 (2014). doi:10.1128/mBio.01130-14.Editor.

Stryer, et al., "Biochemistry." W.H. Freeman. The EMBO Journal vol. 7, No. 7, pp. 1989-1994 (1988).

Sun, et al., "CO 2 enabled process integration for the production of cellulosic ethanol using bionic liquids." The Royal Society of Chemistry. Energy Environ. Sci. vol. 9, pp. 2822-2834 (2016). doi:10.1039/C6EE00913A.

Tai, et al., "Engineering the push and pull of lipid biosynthesis in oleaginous yeast Yarrowia lipolytica for biofuel production." Eng. vol. 15, pp. 1-9 (2013). doi:10.1016/j.ymben.2012.08.007.

Tehlivets, et al. Fatty acid synthesis and elongation in yeast. Institute of Molecular Biosciences, University of Graz, A8010 Graz, Austria. Biochimica et Biophysica Acta 1771, pp. 255-270 (2007). doi:10.1016/j.bbalip.2006.07.004.

Thomas, et al. "Identification of the structural gene for glucose-60phosphate dehydrogenase in yeast. Inactivation leads to a nutritional requirement for organic sulfur." The EMBO Journal. vol. 10, No. 3, pp. 547-553 (1991).

Verho, et al., "Identification of the first fungal NADP-GAPDH from Kluyveromyces latis." Biochemistry. vol. 41, pp. 13833-13838. doi:10.1021/bi0265325, 2002.

Wahlen, et al., "Purification, characterization, and potential bacterial wax production role of an NADPH-dependent fatty aldehyde reductase from Marinobacter aquaeolei VT8." Appl. Environ. Microbiol. vol. 75, pp. 2758-2764 (2009). doi:10.1128/AEM.02578-08.

Willis, et al., "Characterization of a fatty acyl-CoA reuctase from Marinobacter aquaeolei VT8: a bacterial enzyme catalyzing the reduction of fatty acyl-CoA to fatty alcohol." American Chemical Society (ACS). Biochemistry. vol. 50, pp. 10550-10558 (2011). doi:10.1021/bi2008646, 2011.

Xu, et al., "Transforming biomass conversion with ionic liquids: process intensification and the development of a high-gravity, one-pot process for the production of cellulosic ethanol." The Royal Society of Chemistry, Energy Environ. Sci. 9, 1042-1049. doi:10.1039/C5EE02940F, 2016.

Zampar, et al., "Temporal system-level organization of the switch from glycolytic to gluconeogenic operation in yeast." Mol. Syst. Biol. 9, 651. doi:10.1038/msb.2013.11, 2013.

Zhang, et al., "Improving the ethanol yield by reducing glycerol formation using cofactor regulation in *Saccharomyces cerevisiae*." Biotechnol. Lett. vol. 33, pp. 137501380. doi:10.1007/s10529-011-0588-6, 2012.

Zhang, et al., "Enhancing fatty acid production by the expression of regulatory transription facture FadR." Metab. Eng. vol. 14, pp. 653-660. doi:10.1016/j.ymben.2012.08.009, 2011.

Zhou, et al., "Production of fatty acidderived oleochemicals and biofuels by synthetic yeast cell factories." Nature Communications. vol. 7, pp. 11709 (2016). doi:10.1038/ncomms/11709.

Zhu, et al., "Dissolution of cellulose with ionic liquids and its application: a mini-review." Green Chem. vol. 8, p. 325(2006). doi:10.1039/b601395c.

\* cited by examiner

MmFAR1-GFP

YEAST CELLS AND METHODS FOR PRODUCING FATTY ALCOHOLS

CROSS-REFERENCE TO RELATED APPLICATIONS

The application claims priority as a continuation to U.S. patent application Ser. No. 15/979,144, filed May 14, 2018, now U.S. Pat. No. 10,557,152, issued on Feb. 11, 2020, which claims priority to U.S. Provisional Patent Application Ser. No. 62/505,725, filed May 12, 2017, both of which are herein incorporated by reference in their entireties.

STATEMENT OF GOVERNMENTAL SUPPORT

The invention was made with government support under Contract No. DE-AC02-05CH11231 awarded by the U.S. Department of Energy. The government has certain rights in the invention.

REFERENCES TO SUBMISSION OF A SEQUENCE LISTING

This application includes a Sequence Listing as a text file named "2017_097_02_Sequence_Listing_ST25" created Oct. 8, 2018 and containing 4,770 bytes. The material contained in this text file is incorporated by reference in its entirety for all purposes.

FIELD OF THE INVENTION

The present invention is in the field of producing fatty alcohols from engineered yeast cells.

BACKGROUND OF THE INVENTION

Several laboratories have reported on engineering the fatty acid pathway in a microbial yeast such as *Saccharomyces cerevisiae* as a sustainable platform for producing biofuels and other products (Kalscheuer et al., 2006; Runguphan and Keasling, 2013). A range of enzymes and pathways have been heterologously expressed to convert fatty acid thioesters—produced by endogenous fatty acid biosynthesis—into ethyl esters, acids, alcohols, alkanes, methyl ketones, dicarboxylic acids, etc. (Clomburg et al., 2015; Goh et al., 2012; Zhou et al., 2016). Among these products, long-chain fatty alcohols in the C12-C18 range have recently received intense attention due to their value and broad applications in laundry detergents, industrial lubricants and surfactants, medicines and personal care products, and potentially as biofuels (Feng et al., 2015; Liu et al., 2016; Pfleger et al., 2015). In 2016, the worldwide market for fatty alcohols was $3.7 billion and growing, with annual production of more than 2.6 metric tons sourced primarily from fossil fuels (petroleum, or polymerized natural gas) or plant oil crops (triglycerides) processed chemically into alcohols (Gaikwad, 2016). Microbial production, besides providing a more sustainable source, can allow for highly specific chemical modifications (Haushalter et al., 2014) to improve product performance or create new applications in ways that could be difficult or impossible by traditional thermochemical means.

However, low yields and economic competition from mature petrochemical processes hamper widespread adoption of microbial fatty alcohol production. Traditionally, *S. cerevisiae* is the preferred industrial biorefinery yeast due to its genomic and structural robustness, and since existing ethanol-producing fermentation facilities could be retrofitted for another product. Yet yields of fatty alcohols in *S. cerevisiae* stand at less than 2% of the theoretical maximum from glucose (Zhou et al., 2016). Besides product yield, economic viability also depends on the choice of feedstocks. Sugars derived from food crops are cost-prohibitive and divert water and other resources in a period where demand for food and water is expected to increase ~50% by the turn of this century (Connor and Uhlenbrook, 2016). Using lignocellulosic feedstocks derived from agricultural waste or energy crops that do not compete for water and land with food would lower costs and provide maximal $CO_2$ emission offsets (Caspeta and Nielsen, 2013).

SUMMARY OF THE INVENTION

The present invention provides for a genetically modified yeast cell comprising at least six or more of the following modifications: (a) an increased expression of *Mus musculus* fatty acid reductase (FAR) (MmFAR1), or functional fragment thereof; (b) an increased expression of acetyl-CoA carboxylase (ACC1), or functional fragment thereof; (c) an increased expression of fatty acid synthase 1 (FAS1), or functional fragment thereof; (d) an increased expression of fatty acid synthase 2 (FAS2), or functional fragment thereof; (e) a reduced expression of or knocked out for DGA1; (f) a reduced expression of or knocked out for HFD1; (g) a reduced expression of or knocked out for ADH6; (h) an increased expression of a mutant of the bottleneck enzyme encoded by ACC1 insensitive to post-transcriptional and post-translational repression, or functional fragment thereof; (i) a reduced expression of or knocked out for GDH1; and (j) an increased expression of the desaturase encoded by OLE1, or functional fragment thereof.

In some embodiments, the genetically modified yeast cell comprises at least seven or more of the modifications. In some embodiments, the genetically modified yeast cell comprises at least eight or more of the modifications. In some embodiments, the genetically modified yeast cell comprises at least nine or more of the modifications. In some embodiments, the genetically modified yeast cell comprises at least ten or more of the modifications.

In some embodiments, the yeast cell is a *Saccharomyces* cell. In some embodiments, the *Saccharomyces* cell is a *Saccharomyces cerevisiae* cell. In some embodiments, the *Saccharomyces cerevisiae* cell is a cell of the *Saccharomyces cerevisiae* BY4741 strain.

The present invention also provides for a method of constructing the genetically modified yeast cell of the present invention comprising at least six or more of the following steps: (a) introducing a first nucleic acid encoding MmFAR1, or functional fragment thereof, operatively linked to a promoter capable of expressing the MmFAR1 gene product in the yeast cell; (b) introducing a second nucleic acid encoding ACC1, or functional fragment thereof, operatively linked to a promoter capable of expressing the ACC1 gene product in the yeast cell, or replacing the native promoter of ACC1 with a promoter with a higher transcription activity, such as promoter TEF1; (c) introducing a third nucleic acid encoding FAS1, or functional fragment thereof, operatively linked to a promoter capable of expressing the FAS1 gene product in the yeast cell, or replacing the native promoter of FAS1 with a promoter with a higher transcription activity, such as promoter TEF1; (d) introducing a fourth nucleic acid encoding FAS2, or functional fragment thereof, operatively linked to a promoter capable of expressing the FAS2 gene product in the yeast cell or replacing the native promoter of FAS2 with a promoter with a higher transcription activity, such as promoter TEF1; (e) removing all or a portion of the DGA1 gene, or introducing a nucleic acid into the yeast cell targeting the DGA1 gene or its gene product, such that the yeast cell has a reduced amount of activity of the DGA1 gene product; (f) removing all or a portion of the HFD1 gene, or introducing a nucleic acid into the yeast cell targeting the HFD1 gene or its gene product, such that the yeast cell has a reduced amount of activity of the HFD1 gene product; (g) removing all or a portion of the ADH6 gene, or introducing a nucleic acid into the yeast cell targeting the ADH6 gene or its gene product, such that the yeast cell has a reduced amount of activity of the ADH6 gene product; (h) introducing a fifth nucleic acid encoding a mutant of the bottleneck enzyme encoded by ACC1 insensitive to post-transcriptional and post-translational repression, or functional fragment thereof, operatively linked to a promoter capable of expressing the mutant ACC1 gene product in the yeast cell; (i) removing all or a portion of the GDH1 gene, or introducing a nucleic acid into the yeast cell targeting the GDH1 gene or its gene product, such that the yeast cell has a reduced amount of activity of the GDH1 gene product; (j) introducing a sixth nucleic acid encoding OLE1, or functional fragment thereof, operatively linked to a promoter capable of expressing the OLE1 gene product in the yeast cell; and (k) introducing a seventh nucleic acid encoding a second copy of MmFAR1, or functional fragment thereof, operatively linked to a promoter capable of expressing the MmFAR1 gene product in the yeast cell. In some embodiments, alternatively the introducing steps of (e), (f), (g), and/or (i) independently comprise introducing gRNA into the yeast cell, such as using dCAS9, to inhibit each respective gene through gene silencing or antisense or the like.

In some embodiments, two or more of the one to six nucleic acids of the method reside on a single nucleic acid. In some embodiments, the nucleic acid is capable of stable maintenance in the genetically modified yeast cell. In some embodiments, the nucleic acid is a vector capable of stable maintenance in the genetically modified yeast cell. In some embodiments, the nucleic acid introduced into the genetically modified yeast cell causes the stable integration of the nucleic acid in a chromosome of the genetically modified yeast cell. In some embodiments, the OLE1 is a fatty acid-desaturase encoded by OLE1.

The present invention further provides for a method of producing a fatty alcohol from a genetically modified yeast cell comprising: (a) providing a genetically modified yeast cell of the present invention, and (b) growing or culturing the genetically modified yeast cell in a medium such that the genetically modified yeast cell produces one or more fatty alcohols, or a mixture thereof.

In some embodiments, the method further comprises one or more steps of the method of constructing the genetically modified yeast cell of the present invention. In some embodiments, each one liter of the genetically modified yeast cell grown or cultured in the medium produces 0.2, 0.4, 0.6, 0.8, or 1.0 g or more of fatty alcohol. In some embodiments, the growing or culturing step (b) comprises growing or culturing the genetically modified yeast cell in a fed-batch or continuous culture. In some embodiments, each one liter of the genetically modified yeast cell grown or cultured in the fed-batch or continuous culture produces 1.0, 2.0, 3.0, 4.0, 5.0, or 6.0 g or more of fatty alcohol. A production of 6.0 g/L of fatty alcohol corresponds to about 20% of the maximum theoretical yield from glucose.

In some embodiments, the medium comprises a carbon source produced from a biomass, such as a lignocellulosic feedstock. In some embodiments, the carbon source produced from the biomass is obtained by deconstructing a non-food crop using a cholinium-based renewable ionic liquid (IL). In some embodiments, the medium is fed a constant from about 1.5 g/hr to about 3.0 g/hr glucose, or pulse-fed about 1 g/hr glucose.

Four heterologous fatty acid reductases are compared and activity and ER localization is found high using a *Mus musculus* FAR. From screening an additional 21 single-gene edits, the following successful strategies to improve titer are identified: a strain containing eleven genetic modifications compared to the parent BY4741 strain produced 1.2 g/L fatty alcohols in shake flasks.

High-level production from feedstocks produced from non-food crops and cholinium-based renewable bionic ILs reaching a titer of 0.7 g/L in shake flasks are demonstrated. Scale-up fermentation and exploring alternative feeding strategies aimed at limiting overflow metabolism, achieving a titer of 6.0 g/L in a 2-L, fed-batch bioreactor, are demonstrated. These titers are the highest for fatty alcohols reported to date for *S. cerevisiae*. This is the first report of a bioproduct produced by yeast from feedstocks derived solely from biomass.

In some embodiments, the fatty alcohol is a fatty alcohol in the C12-C18 range. Fatty alcohols in the C12-C18 range are used in personal care products, lubricants, and potentially biofuels.

The present invention relates to genetic modifications to yeast to produce high levels of long-chain alcohols in the C12-C18 range containing terminal alcohol groups. The production levels are in the 1-10 g/L range and are the highest to date in engineered *Saccharomyces cerevisiae*. This invention also relates to high-level production using feedstocks derived from lignocellulose, such as, *Sorghum* or switchgrass. This invention relates to using lignocellulosic biomass pre-treated with ionic liquids as the sole carbon source for fatty alcohol production by the engineered microorganisms. The technical problems overcome to achieve this high-level production are screening dozens of genetic modifications to find changes that led to increased production and/or growth of the engineered strains. These genetic changes include screening heterologous fatty acid reductase (FAR) enzymes and finding highest activity and endoplasmic reticulum localization from a *Mus musculus* FAR. In some embodiments, the genetically modified yeast cell comprises an increased FAR expression; deleting competing reactions encoded by DGA1, HFD1, and ADH6; overexpressing a mutant acetyl-CoA carboxylase; limiting NADPH and carbon usage by the glutamate dehydrogenase encoded by GDH1; and overexpressing the fatty acid-desaturase encoded by OLE1. In some embodiments, the genetically modified yeast cell produces 1.0, 1.1, 1.2, or 1.3 g/L or more fatty alcohols in shake flasks, and 6.0 g/L in fed-batch fermentation, corresponding to about 20% of the maximum theoretical yield from glucose, the highest titers and yields reported to date in *S. cerevisiae*. In some embodiments, the genetically modified yeast cell is grown using a carbon source produced from lignocellulosic feedstocks derived from ionic-liquid treated switchgrass and *Sorghum*, reaching 0.7 g/L in shake flasks.

Fatty alcohols can be used as industrial lubricants, in personal care products (e.g., conditioners, creams, lotions, shampoos), and as biofuels. Fatty alcohols produced from microbial cell factories from lignocellulosic biomass are renewable. Alternative petroleum-based sourcing is not renewable and oil crops compete with food for land and water. Lignocellulosic feedstocks (e.g., switchgrass, *Sorghum*) can be converted to fatty alcohols at high titer through the present invention and provide a green sourcing for these important products.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
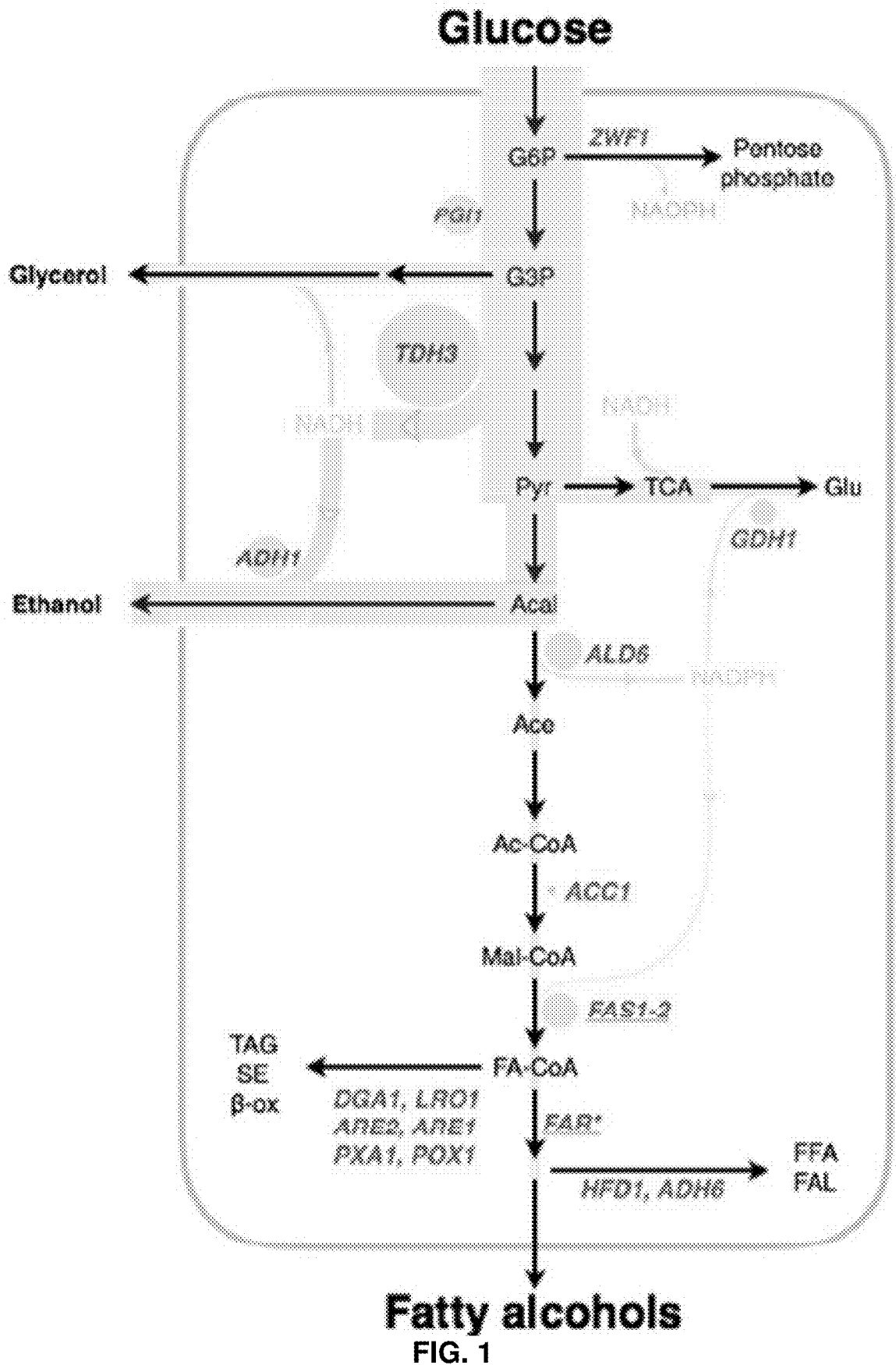
FIG. 1. Schema for fatty chemical engineering showing metabolic flux and protein levels of previous first-generation producer. The highest-titer chemical producer strain (yL401) from our previous study (Runguphan and Keasling, 2013) was analyzed by shotgun proteomics (Batth et al., 2012) and metabolic flux analysis (García Martín et al., 2015) to identify targets for engineering increased production. Carbon flux is indicated by orange lines, the width proportional to net normalized flux through the corresponding reaction. Fluxes of reducing equivalents (from NADH or NADPH) are indicated by blue lines (with the thickness proportional to molar flux, which is not on the same scale as carbon flux). Fluxes to $CO_2$, biomass, and minor products are not shown. Enzyme levels are indicated by the areas of the red circles. The genes underlined are overexpressed in the first-generation strain. *Fatty acid reductase (FAR) is used to produce fatty alcohols from fatty acyl-CoA produced by fatty acid biosynthesis, with the three fatty acid biosynthetic genes overexpressed in the first-generation producer strain. The flux and proteomics analysis is performed on a free fatty acid producer, containing a thioesterase rather than a FAR.

Before the invention is described in detail, it is to be understood that, unless otherwise indicated, this invention is not limited to particular sequences, expression vectors, enzymes, yeast microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The term "about" refers to a value including 10% more than the stated value and 10% less than the stated value.

The following abbreviations are used herein:
Ac-CoA Acetyl-Coenzyme A, cytoplasmic
Acal Acetaldehyde
ACC1 Acetyl-CoA carboxylase (overexpressed)
ACC1** ACC1 with two mutations abolishing post-translational phosphorylation inhibition
Ace Acetate
ADH1 Alcohol dehydrogenase (ethanol-forming, NAD-dependent)
ADH6 Medium chain alcohol dehydrogenase
ALD6 Aldehyde dehydrogenase (cystolic, NADP+-dependent)
ARE1 Acyl-CoA:sterol acyltransferase
ARE2 Acyl-CoA:sterol acyltransferase
BcGapN B. cereus Glyceraldehyde-3-phosphate dehydrogenase (Non-phosphorylating, NADP-dependent)
DGA1 Diacylglycerol acyltransferase
FA-CoA Fatty acyl-CoA
FAL Fatty aldehyde
FAR Fatty acid reductase (Fatty acyl-CoA reductase, NADPH-dependent)
FAS 1 Fatty acid synthase (subunit beta)
FAS2 Fatty acid synthase (subunit alpha)
FFA Free fatty acid
G3P Glyceraldehyde 3-phosphate
G6P Glucose 6-phosphate
GDH1 Glutamate dehydrogenase (NADPH-dependent)
GFP A. victoria Green fluorescent protein
HFA1cvt Mitochondrial acetyl-CoA carboxylase with mitochondrial targeting signal deleted
HFD1 Fatty aldehyde dehydrogenase
INO2 Transcription factor, derepression of phospholipid biosynthetic genes
KlGapDH K. lactis Glyceraldehyde-3-phosphate dehydrogenase (NADP-dependent)
LRO1 Diacylglycerol acyltransferase
Mal-CoA Malonyl-CoA
MBP E. coli maltose-binding protein
NADH Nicotinamide adenine dinucleotide (reduced form)
NADPH Nicotinamide adenine dinucleotide phosphate (reduced form)
OLE1 Delta(9) fatty acid desaturase
OLI1 Transcription factor, negative regulation of phospholipid biosynthetic genes
PGI1 Phosphoglucose isomerase
POX1 Fatty-acid coenzyme A oxidase
PXA1 Peroxisomal fatty acyl-CoA importer (with PXA2)
Pvr Pyruvate
RPD3 Histone deacetylase
SE Steryl esters
TAG Triacylglycerides
TCA Tricarboxylic acid cycle
TDH3 Glyceraldehyde-3-phosphate dehydrogenase (NAD-dependent)
ZWF1 Glucose-6-phosphate dehydrogenase (NADP-dependent)

The term "heterologous DNA" as used herein refers to a polymer of nucleic acids wherein at least one of the following is true: (a) the sequence of nucleic acids is foreign to (i.e., not naturally found in) a given yeast microorganism; (b) the sequence may be naturally found in a given yeast microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Specifically, the present invention describes the introduction of an expression vector into a yeast microorganism, wherein the expression vector contains a nucleic acid sequence coding for an enzyme that is not normally found in a yeast microorganism. With reference to the yeast microorganism's genome, then, the nucleic acid sequence that codes for the enzyme is heterologous.

The terms "expression vector" or "vector" refer to a compound and/or composition that transduces, transforms, or infects a yeast microorganism, thereby causing the cell to express nucleic acids and/or proteins other than those native to the cell, or in a manner not native to the cell. An "expression vector" contains a sequence of nucleic acids (ordinarily RNA or DNA) to be expressed by the yeast microorganism. Optionally, the expression vector also comprises materials to aid in achieving entry of the nucleic acid into the yeast microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a yeast microorganism and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "transduce" as used herein refers to the transfer of a sequence of nucleic acids into a yeast microorganism or cell. Only when the sequence of nucleic acids becomes stably replicated by the cell does the yeast microorganism or cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a yeast microorganism, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

The terms "isolated" or "biologically pure" refer to material that is substantially or essentially free of components that normally accompany it in its native state or free of components from a yeast cell or culture medium from which the material is obtained.

The term "operably linked" refers to a functional linkage between a nucleic acid expression control sequence (such as a promoter) and a second nucleic acid sequence, wherein the expression control sequence directs transcription of the nucleic acid corresponding to the second sequence.

The term "functional fragment" refers to an enzyme that has an amino acid sequence that is at least 70%, 75%, 80%, 85%, 90%, 95% or 99% identical to the amino acid sequence of any one of the enzymes described in this specification or in an incorporated reference. The functional fragment retains amino acids residues that are recognized as conserved for the enzyme. The functional fragment may have non-conserved amino acid residues replaced or found to be of a different amino acid, or amino acid(s) inserted or deleted, but which does not affect or has insignificant effect on the enzymatic activity of the functional fragment. The functional fragment has an enzymatic activity that is identical or essentially identical to the enzymatic activity any one of the enzymes described in this specification or in an incorporated reference. The functional fragment may be found in nature or be an engineered mutant thereof. The mutant may have one or more amino acids substituted, deleted or inserted, or a combination thereof, as compared to the enzyme described in this specification or in an incorporated reference.

The amino acid sequence of *Mus musculus* fatty acid reductase (FAR) is as follows:

```
                                              (SEQ ID NO: 1)
        10         20         30         40
MVSIPEYYEG KNILLTGATG FLGKVLLEKL LRSCPRVNSV 50         60         70         80
YVLVRQKAGQ TPQERVEEIL SSKLFDRLRD ENPDFREKII 90        100        110        120
AINSELTQPK LALSEEDKEI IIDSTNVIFH CAATVRFNEN 130        140        150        160
LRDAVQLNVI ATRQLILLAQ QMKNLEVFMH VSTAYAYCNR 170        180        190        200
KHIDEVVYPP PVDPKKLIDS LEWMDDGLVN DITPKLIGDR 210        220        230        240
PNTYIYTKAL AEYVVQQEGA KLNVAIVRPS IVGASWKEPF 250        260        270        280
PGWIDNFNGP SGLFIAAGKG ILRTMRASNN ALADLVPVDV 290        300        310        320
VVNTSLAAAW YSGVNRPRNI MVYNCTTGST NPFHWGEVEY 330        340        350        360
HVISTFKRNP LEQAFRRPNV NLTSNHLLYH YWIAVSHKAP 370        380        390        400
AFLYDIYLRM TGRSPRMMKT ITRLHKAMVF LEYFTSNSWV 410        420        430        440
WNTDNVNMLM NQLNPEDKKT FNIDVRQLHW AEYIENYCMG 450        460        470        480
TKKYVLNEEM SGLPAARKHL NKLRNIRYGF NTILVILIWR 490        500        510
IFIARSQMAR NIWYFVVSLC YKFLSYFRAS STMRY
```

In some embodiments, the yeast cell in its unmodified form has a native enzyme of one of the enzymes described herein. In some embodiments, the gene encoding the enzyme of one of the enzymes described herein is deleted or modified such that expression of the gene is reduced or eliminated. In some embodiments, the yeast cell has a reduced capability to catabolize, metabolize, or modify the fatty alcohol.

The nucleic acid constructs of the present invention comprise nucleic acid sequences encoding one or more of the subject enzymes. The nucleic acid of the subject enzymes are operably linked to promoters and optionally control sequences such that the subject enzymes are expressed in a yeast cell cultured under suitable conditions. The promoters and control sequences are specific for each yeast cell species. In some embodiments, expression vectors comprise the nucleic acid constructs. Methods for designing and making nucleic acid constructs and expression vectors are well known to those skilled in the art.

Sequences of nucleic acids encoding the subject enzymes are prepared by any suitable method known to those of ordinary skill in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (e.g., in Matteuci et al. (1980) *Tet. Lett.* 521:719; U.S. Pat. Nos. 4,500,707; 5,436,327; and 5,700,637). In addition, the desired sequences may be isolated from natural sources by splitting DNA using appropriate restriction enzymes, separating the fragments using gel electrophoresis, and thereafter, recovering the desired nucleic acid sequence from the gel via techniques known to those of ordinary skill in the art, such as utilization of polymerase chain reactions (PCR; e.g., U.S. Pat. No. 4,683,195).

Each nucleic acid sequence encoding the desired subject enzyme can be incorporated into an expression vector. Incorporation of the individual nucleic acid sequences may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single stranded ends that may be annealed to a nucleic acid sequence having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired nucleic acid sequence are often cleaved with the same restriction enzyme, thereby assuring that the ends of the expression vector and the ends of the nucleic acid sequence are complementary to each other. In addition, DNA linkers may be used to facilitate linking of nucleic acids sequences into an expression vector.

A series of individual nucleic acid sequences can also be combined by utilizing methods that are known to those having ordinary skill in the art (e.g., U.S. Pat. No. 4,683, 195).

For example, each of the desired nucleic acid sequences can be initially generated in a separate PCR. Thereafter, specific primers are designed such that the ends of the PCR products contain complementary sequences. When the PCR products are mixed, denatured, and reannealed, the strands having the matching sequences at their 3' ends overlap and can act as primers for each other. Extension of this overlap by DNA polymerase produces a molecule in which the original sequences are "spliced" together. In this way, a series of individual nucleic acid sequences may be "spliced" together and subsequently transduced into a yeast microorganism simultaneously. Thus, expression of each of the plurality of nucleic acid sequences is effected.

In some embodiments, the yeast cells of the present invention are genetically modified in that heterologous nucleic acid have been introduced into the yeast cells, and as such the genetically modified yeast cells do not occur in nature. The suitable yeast cell is one capable of expressing a nucleic acid construct encoding the enzyme(s) described herein. The gene encoding the enzyme may be heterologous to the yeast cell or the gene may be native to the yeast cell but is operatively linked to a heterologous promoter and one or more control regions which result in a higher expression of the gene in the yeast cell. Each enzyme described herein can be native or heterologous to the yeast cell. Where the enzyme is native to the yeast cell, the yeast cell is genetically modified to modulate expression of the enzyme. This modification can involve the modification of the chromosomal gene encoding the enzyme in the yeast cell or a nucleic acid construct encoding the gene of the enzyme is introduced into the yeast cell. One of the effects of the modification is the expression of the enzyme is modulated in the yeast cell, such as the increased expression of the enzyme in the yeast cell as compared to the expression of the enzyme in an unmodified yeast cell.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

Engineering High-Level Production of Fatty Alcohols by *Saccharomyces Cerevisiae* from Lignocellulosic Feedstocks Fatty alcohols in the C12-C18 range are used in personal care products, lubricants, and potentially biofuels. These compounds can be produced from the fatty acid pathway by a fatty acid reductase (FAR), yet yields from the preferred industrial yeast *Saccharomyces cerevisiae* remain under 2% of the theoretical maximum from glucose. Titer and yield of fatty alcohols are improved using an approach involving quantitative analysis of protein levels and metabolic flux, engineering enzyme level and localization, pull-push-block engineering of carbon flux, and cofactor balancing. Four heterologous FARs are compared, finding highest activity and endoplasmic reticulum localization from a *Mus musculus* FAR. After screening an additional twenty-one single-gene edits, increasing FAR expression is identified; deleting competing reactions encoded by DGA1, HFD1, and ADH6; overexpressing a mutant acetyl-CoA carboxylase; limiting NADPH and carbon usage by the glutamate dehydrogenase encoded by GDH1; and overexpressing the fatty acid-desaturase encoded by OLE1 as successful strategies to improve titer. The final strain produced 1.2 g/L fatty alcohols in shake flasks, and 6.0 g/L in fed-batch fermentation, corresponding to ~20% of the maximum theoretical yield from glucose, the highest titers and yields reported to date in *S. cerevisiae*. High-level production from lignocellulosic feedstocks derived from ionic-liquid treated switchgrass and *Sorghum* is demonstrated, reaching 0.7 g/L in shake flasks. Altogether, these results represent progress towards efficient and renewable microbial production of fatty acid-derived products.

Titers and yields of fatty alcohols produced by *S. cerevisiae* are improved and demonstrate high-level production from lignocellulosic biomass hydrolysates. This approach included quantitative analysis of metabolic flux and global protein expression to identify pathway bottlenecks in a first-generation fatty chemical producer strain and identify genetic modifications for maximizing pathway flux. Among these modifications, four heterologous fatty acid reductases—which convert fatty acyl-CoA into fatty alcohols—are compared exploring enzyme expression level and subcellular localization. Additionally, over two dozen genetic modifications for improvements in fatty alcohol production are screened and combined beneficial changes into a strain that produced fatty alcohols at high titers and yields. To develop an efficient bioprocess with this strain, fatty alcohol production from lignocellulosic feedstocks is evaluated in a one-pot process using cholinium-based ionic liquids. Lastly, successful scale-up in 2 L fed-batch bioreactors combined with an initial exploration of alternative substrate feeding strategies is demonstrated to maximize titer and yield.

Materials and Methods

Generating Strains

All yeast strains in this study are derived from *Saccharomyces cerevisiae* BY4741 (Brachmann et al., 1998), to which the native promoters driving ACC1, FAS1, and FAS2 are replaced with the TEF1 promoter as previously reported, generating strain WRY1 (Runguphan and Keasling, 2013). All subsequent strains (Table 1) are created via Cas9-aided homologous recombination using the software tool CASdesigner (the webpage of casdesigner.jbei.org) to design integration cassettes and following a previously reported, cloning-free methodology (Reider Apel et al., 2016). Briefly, integration cassettes containing 1-kb flanking homology regions targeting a chosen genomic locus are constructed by PCR-amplifying donor DNA fragments using primers generated by CASdesigner, then co-transformed with a Cas9-gRNA plasmid (pCut) targeting the chosen genomic locus. CASdesigner primers provide 30-60 nt of inter-fragment homology allowing 1-5 separate fragments to assemble via homologous recombination in vivo. pCuts targeting empty genomic loci (e.g., 208a, 1622b) are available pre-cloned, and pCuts targeting new sites (e.g., for deletions) are assembled in vivo from a linear backbone and a linear PCR fragment containing the new gRNA sequence, as described previously (Reider Apel et al., 2016). New gRNA sequences are chosen using DNA2.0 (the webpage of dna20.com/eCommerce/cas9/input) or CHOP-CHOP (the webpage of chopchop.rc.fas.harvard.edu) (Montague et al., 2014). To generate donor DNA fragments, native sequences—e.g., chromosomal homology regions, promoters—are amplified from BY4741 genomic DNA, while heterologous sequences—e.g., fatty acid reductase coding sequences—are amplified from synthetic gene blocks codon-optimized (for expression in S. cerevisiae) and synthesized by Integrated DNA Technologies (the webpage of idtdna.com). All PCRs used Phusion Hot Start II DNA polymerase (the webpage of thermofisher.com, cat. F549L).

Transformations are performed via heat-shock (Gietz and Woods, 2002) using ~200 ng pCut, ~1 ug donor DNA per sample, and 20 min heat shock. For assembling a pCut targeting a new site by homologous recombination, 200 ng linear pCut backbone and 500 ng of a 1-kb fragment containing the gRNA sequence are used, as described (Reider Apel et al., 2016). For multi-site integrations, 200 ng total linear pCut backbone, and the same amounts of gRNA fragment and donor DNA for each site are used as one would have for a single integration. Colonies are screened by PCR directed at the target locus, and for integrations, one representative colony sequenced. Three to four biological replicates are analyzed for each strain.

Media and Culture Conditions

Selective agar plates used for transformations are purchased from Teknova (the webpage for: teknova.com, cat. C3080). Liquid selective medium used to grow transformants contains 0.2% (w/v) complete supplement mixture (CSM) lacking uracil, 0.67% yeast nitrogen base, and 2% dextrose. Nonselective medium contains 1% yeast extract, 2% peptone (Difco cat. 288620 and 211677, respectively), and either 2% dextrose (YPD) or 2% galactose and 0.2% dextrose (YPG). Nonselective agar YPD plates are purchased from Teknova (cat. Y100). Cultures are grown in plastic 96-deep well plates, 24-deep well plastic plates (CWR cat. 89080-534), glass test tubes, or 250-ml baffled flasks, as indicated in the results section. Production cultures are overlaid with dodecane, the latter spiked with 200 mg/L methyl nonadecanoate (sigma cat. N5377) as an internal standard. Plastic plates are covered with aeraseal film and shaken at 800 rpm in a Multitron shaker. Glass tubes and baffled flasks are shaken at 200 rpm. All strains are grown at 30° C.

Shotgun Proteomics

Strains for proteomics analysis are grown in YPD overnight, then back-diluted 1:100 into 5 ml fresh YPD and grown 8 hrs. For each sample, the entire culture volume is centrifuged at 3000×g on a table-top centrifuge, decanted, and the pellet flash-frozen in liquid nitrogen and stored at −80° C. until preparation as described (Batth et al., 2012). Briefly, cell pellets are lysed in urea and bead-beaten. The lysate is reduced using tris(2-carboxyethyl)phosphine (sigma cat. C4706), then alkylated using iodoacetamide (sigma cat. 11149), trypsinized, desalted on spin columns, and finally suspended in a buffer of 0.1% formic acid to a final concentration of 2 μg protein/μl. Peptide data are acquired using an Agilent 1290 liquid chromatography system coupled to an Agilent 6550 QTOF mass spectrometer and analyzed using Agilent MassHunter version B.06.00. Resultant data files are searched with Mascot version 2.3.02 (the webpage of matrixscience.com) then filtered and validated using Scaffold version 4.4.0 (the webpage of proteomesoftware.com).

Metabolic Flux Analysis Using $^{13}$C-Labeled Glucose

Metabolic flux analysis is performed as previously reported (García Martín et al., 2015; Ghosh et al., 2016). Briefly, strains are grown in 250-ml shake flasks in 25 ml medium containing $^{13}$C-labeled glucose (sigma cat. 407-622-22-9 and 110187-42-3) and sampled at exponential phase near OD 1.0. Sampling included filtering media for high-performance liquid chromatography (HPLC) to quantify extracellular metabolites, ethyl acetate extraction followed by gas chromatography-mass spectrometry (GC-MS) to quantify fatty acid products, and methanol/chloroform extraction followed by liquid chromatography-mass spectrometry (LC-MS/MS) to analyze $^{13}$C labeling in metabolites. These $^{13}$C labeling data are used to constrain the S. cerevisiae genome-scale model iMM904 (Mo et al., 2009) using two-scale $^{13}$C Metabolic Flux Analysis (García Martín et al., 2015; Ghosh et al., 2016) with the open-source, python-based JBEI Quantitative Metabolic Modeling library (the webpage of github.com/JBEI/jqmm) to model the metabolic flux distribution.

Fatty Alcohol Production Cultivations

Initial production cultivations are performed as described (Runguphan and Keasling, 2013). Briefly, three to four biological replicates are each inoculated into 5 ml medium in glass test tubes overnight, then back-diluted 1:100 into 5 ml of the same medium, overlaid with 0.5 ml dodecane (spiked with internal standard), and shaken at 200 rpm for three days. The overlay is collected and centrifuged at 3000×g, and 10 μl of the top organic phase added to 90 μl ethyl acetate in a GC-MS vial containing a glass insert for subsequent analysis. This method of cultivation and sampling is used to compare the fatty acid reductases, in YPD, and for initial cultivations of strain yL405 in biomass hydrolysates and other media.

To screen genetically edited strains for improvements in fatty alcohol production, the appearance of precipitated fatty alcohols in some strains (FIG. 3C) prevented sampling the liquid overlay. Instead, four biological replicates are inoculated into 1 ml YPG in 24-deep well plates and grown overnight, then back-diluted 1:100 into 1 ml YPG, overlaid with 0.2 ml dodecane (spiked with internal standard), covered with aeraseal, and shaken at 800 rpm for three days. Then, 100 μl of culture is added to 800 μl ethyl acetate in 1.6-ml eppendorf tubes, vortexed at maximum setting 30 min, centrifuged at 10,000×g on a table-top centrifuge, and 100 μl of the top organic phase added to a GC-MS vial containing a glass insert for analysis. This method of cultivation and sampling is used to compare strain yL405 to all subsequent genetically modified strains.

To characterize production of the final highest-producer strain yL434, four biological replicates are grown in 1 ml corresponding medium overnight in glass test tubes, then back-diluted 1:100 into 10 ml of the same medium in 250-ml baffled flasks, overlaid with 2 ml dodecane (spiked with internal standard), and shaken at 200 rpm for three days. Then, 100 μl culture is extracted with ethyl acetate and processed into GC-MS vials as described immediately above. This method of cultivation and sampling is used to compare production of yL434 in YPG, YPD, and YPBiomass media (see Preparation of biomass hydrolysates).

Fed Batch 2 L-Scale Bioreactor Fermentations

Fed-batch fermentations are performed in Sartorius 2 L bioreactors equipped Sartorius BIOSTAT B Plus control units at the Advanced Biofuels Process Demonstration Unit (ABPDU, Lawrence Berkeley National Laboratory, Emeryville, Calif.). The seed strain is inoculated in 500 ml YPD in a 1-L flask and grown overnight to an OD of 4.3. Each bioreactor is loaded with 900 ml YPD, 100 ml inoculum, and 200 ml dodecane (spiked with internal standard). Temperature is maintained at 30° C. via water flow through the reactor jacket. The pH is maintained at 5.0 by auto-dispensing a base solution (2N $NH_4OH$). Dissolved oxygen is maintained at 20% via stirring from 400 to 800 rpm (primary cascade), then sparging air from 1 vvm (volume of air per volume of liquid per minute) to 1.5 vvm (secondary cascade). The feed contained 500 g/L glucose, 10 g/L yeast extract, 10 g/L $(NH_4)_2SO_4$, 8 g/L $KH_2PO_4$, 4 g/L $MgSO_4$, 0.8 g/L NaCl, and 0.5 g/L $CaCl_2$ and is added as described in the results section.

GC-MS and Extracellular Metabolite Analysis

Samples for GC-MS analysis of fatty alcohol content are analyzed on an Agilent 7890A GC equipped with an Agilent 5975 MS detector and an Agilent DB-5MS column. The inlet is set to 300° C., flow at 1 mL/min; the oven to 150° C. for 2 min, then ramped at 30° C./min to 250° C., and held for 2 min. The solvent delay is set to 4 min (or as required to avoid the dodecane peak). An authentic hexadecanol standard (Sigma catalog W255408) is used to determine titer. Extracellular metabolites are analyzed on an automated photometric Gallery Analyzer following the manufacturer's instructions.

Preparation of Biomass Hydrolysates Using Renewable Liquids

Switchgrass (*Panicum virgatum*) and Sorghum (*Sorghum bicolor*) are kindly provided by Idaho National Laboratory. The air-dried biomass is milled using a 40-mesh screen, sieved to the nominal sizes of 40-60 mesh (250-400 μm), and air-dried until the moisture is <10%. The resulting biomass is converted into fermentable sugars in a one-pot, two-step process consisting of biomass pretreatment using cholinium-based IL followed by enzymatic hydrolysis, modified from a previously reported procedure (Xu et al., 2016). Briefly, 20 g dry biomass is mixed with an IL solution containing 20 g IL and 160 g water. The ILs used are cholinium lysinate, cholinium alpha-ketoglutarate, or cholinium aspartate. The 200-g mixture is thoroughly mixed and loaded in a 500-mL Parr reactor and heated to 140° C. for 3 hrs. The reactor is then cooled to room temperature using cooling water, and all the pretreated biomass slurry transferred to a filter membrane for solid-liquid separation. The solid fraction is collected, mixed with distilled water, and pH-adjusted to 5 with HCl. The weight of the mixture after pH adjustment is adjusted to 200 g with distilled water, and A the content transferred into a 1-L shake flask for saccharification. The saccharification is carried out at 50° C. and pH 5 using Novozymes enzyme mixtures Cellic® CTec2 and HTec2, with an enzyme dosage of 20 mg protein per grain glucan and 2 mg protein per gram xylan, respectively. The resulting slurry is filtered using a 0.2-um filter and used to dissolve 10 g/L yeast extract and 20-g/L peptone, making yeast extract-peptone-biomass hydrolysate media. In the results, YPBiomass refers to *Sorghum* treated with cholinium aspartate.

Microscopy

Strains for microscopy are grown in 5 ml YPD overnight, then back-diluted 1:100 into the same medium and grown 3-6 hrs at 200 rpm and 30° C. Then, 1 ml of culture volume is centrifuged at 10,000×g on a table-top centrifuge, washed with 1× water, and imaged using a Zeiss LSM 710 confocal system mounted on a Zeiss inverted microscope with a 63× objective and processed using Zeiss Zen software.

Results and Discussion

Quantitative Analysis of Metabolic Flux and Global Protein Levels in First-Generation Fatty Chemical Producer This work began with a quantitative analysis of metabolic fluxes and global protein levels to characterize this first-generation fatty chemical producer strain and identify possible strategies to improve production. In a previous report, the native promoters driving the three fatty acid biosynthetic genes ACC1, FAS1, and FAS2 was replaced with the strong TEF1 promoter and added terminal enzymes to produce ~100 mg/L fatty alcohols (using a FAR from *Mus musculus*) and ~400 mg/L free fatty acids (using the thioesterase TesA from *Escherichia coli*, and deleting the fatty acyl-CoA ligases encoded by FAA1 and FAA4) (Runguphan and Keasling, 2013). In this study, TesA is chromosomally integrated, expressing it from the TEF1 promoter, and analyzed the resulting strain, yL401, using metabolic flux analysis and global proteomics to identify bottlenecks in the biosynthetic pathway. Modeling metabolic fluxes allowed us to identify how substrates and cofactors involved in fatty chemical production are used and produced by other cellular processes and thus identify possible targets for genetic modification. Layering global protein expression data on top of the flux analysis allowed us to identify genes whose differential expression may provide clues into cellular responses to the fatty chemical pathway, as well as a check on expression levels of enzymes in the fatty acid biosynthetic pathway, or along metabolic routes one may wish to engineer.

To quantify global protein expression, shotgun proteomics on yL401 is performed as well as its un-engineered parent, BY4741. For both strains, many of the most highly expressed proteins—detected at between ~0.5% and ~1.4% of total soluble protein—are glycolytic enzymes (Eno2p, Tdh3p, Tdh2p, Eno1p, Pgk1p), heat shock proteins (Ssa1p, Ssa2p, Ssb1p, Ssb2p), translation elongation factors (Yef3p and Tef1p), and alcohol dehydrogenase 1 (Adh1p). As expected, proteins with increased expression in yL401 included the three fatty acid biosynthetic enzymes Acc1p, Fas1p, and Fas2p (expressed chromosomally from the TEF1 promoter). Neither FAS subunit is detectable in BY4741, yet both reached ~0.25% of soluble protein in yL401. Acc1p is also undetectable in BY4741, but in yL401 reached only ~0.02% of soluble protein. Strain yL401 also showed increased expression of several ribosomal and translation-initiation proteins (including Rpl3p, Cdc33p, Mnp1p, and Rpl39p), all induced 2-7 fold relative to BY4741 but remaining under 0.05% of total soluble protein. Proteins with decreased expression in yL401 included several amino acyl-tRNA ligases (Grs1p, Gln4p) and interestingly, the retrotransposon Ty1 Gag-Pol protein (which dropped by half from 0.17% of soluble protein in BY4741). Proteins expressed at intermediate levels in both strains included the cytosolic NADP-dependent acetaldehyde dehydrogenase (Ald6p); the other four ALD isoenzymes—two are cytosolic and NAD-dependent, the other two mitochondrial—are either not detected or found at nominal levels (less than 0.05% of total protein). Of pentose phosphate pathway enzymes, glucose-6-phosphate dehydrogenase (Zwf1p), the first and rate-limiting enzyme in the pentose phosphate pathway, is not detected (Thomas et al., 1991), but did observe several other enzymes involved in the pathway, e.g., Gnd1p. None of the enzymes involved in the tricarboxylic acid (TCA) cycle or glyoxylate cycle are detected at appreciable levels. Of amino acid biosynthesis enzymes, glutamate dehydrogenase (GDH) isoenzyme 1 is the most highly expressed at 0.12% of total soluble protein.

To model the metabolic flux distribution in yL401, metabolite levels is measured and $^{13}C$ labeling patterns and used the JBEI Quantitative Metabolic Modeling library (García Martín et al., 2015) to model flux through genome-scale model iMM904 (Mo et al., 2009), adding fatty acyl thioesterase reactions (EC number 3.1.2.2). The reconstruction shows carbon from glucose mostly following glycolysis, then the pyruvate dehydrogenase (PDH) bypass from pyruvate to acetaldehyde, and lastly to ethanol (FIG. 1). At high glucose levels, yeast primarily ferments carbon via the PDH bypass rather than oxidize it via mitochondrial respiration, a well-documented phenomenon known as the Crabtree Effect (Zampar et al., 2013). Branching from central carbon metabolism, this reconstruction shows the metabolic route to this product: some of the acetaldehyde is converted to acetate, then acetyl-CoA, malonyl-CoA, and lastly fatty acyl-CoA and derived chemicals. From acetaldehyde, only ~16% of the carbon flux is converted to acetate; the rest to ethanol (by alcohol dehydrogenase, ADH). The production of ethanol is a mechanism to recycle the large flux of NADH produced by glyceraldehyde-3-phosphate dehydrogenase (GapDH), since respiratory consumption of NADH is repressed. The other main non-respiratory mechanism to recycle NADH is to produce glycerol; ~14% of carbon entering glycolysis is routed to this side product. This NADH/NAD$^+$ flux is independent of the other cofactor pool, NADPH/NADP$^+$, which is used in several anabolic reactions including fatty acid biosynthesis (two NADPH are consumed per two carbons added to the growing fatty acid chain). Yeast maintain [NAD$^+$]/[NADH] >>1, and [NADP$^+$/NADPH]<1, such that the cofactor concentration gradients favor reduction of NAD$^+$ for NADH/NAD$^+$-dependent reactions, and oxidation of NADPH for NADPH/NADP$^+$-dependent reactions. This reconstruction shows most NADPH being produced by ALD (~67%), with only a small amount (~25%) from the pentose phosphate pathway. The vast majority of all NADPH is consumed by GDH (~60%) and fatty acid biosynthesis (~40%). Altogether, on a basis of carbon entering from glucose, ~33% is routed to ethanol, ~20% to CO$_2$, ~14% to glycerol, ~2% to acetate, ~16% to biomass, and ~15% to fatty acid product.

The proteomics and flux results allowed us to identify possible bottlenecks or imbalances in the pathway. For example, that Ald6p is the predominant ALD isoform means flux through this reaction produces NADPH—rather than NADH if another ALD isoenzyme are prevalent. Following the carbon flux to the product, on a basis of one acetyl-CoA, the stoichiometry is 0.5× Glucose+1.38×ATP+1.25×NADPH−1 NADH=0.125× C$_{16}$FOH (ADP, NADP$^+$, NAD$^+$, H$^+$, and CO$_2$ not included for simplicity). Even though ALD flux produces NADPH, the metabolic route from glucose to fatty alcohol requires additional NADPH and produces excess NADH, an imbalance sought to be remediate (discussed in a later section). First, however, increasing carbon flux into fatty alcohol production by pull-push-block engineering is focused upon: "pulling" on the pathway by overexpressing the terminal enzyme; "pushing" by overexpressing enzymes to overcome bottlenecks on the metabolic route to the product; and "blocking" unwanted consumption of products or intermediates by deleting genes catalyzing undesirable reactions (Tai and Stephanopoulos, 2013).

TABLE 1

Strains. The following strains are available from the JBEI registry (webpage for: public-registry.jbei.org)

| Strain | yL# | Parent (additional genetic changes) | Reference |
|---|---|---|---|
| BY4741 | 7 | MATa, his3Δ1, leu2Δ0, met15Δ0, ura3Δ0 | Runguphan et al., 2013 |
| WRY1 | 400 | BY4741 (acc1::P$_{TEF1}$-ACC1, fas1::P$_{TEF1}$-FAS1, fas2::P$_{TEF1}$-FAS2) | Runguphan et al., 2013 |
| TesA | 401 | WRY1 (208a::P$_{TEF1}$-EcTesAcyt-T$_{CYC1}$, faa1Δ, faa4Δ) | |
| MaFAR2 | 402 | WRY1 (208a::P$_{TEF1}$-MaFAR2-T$_{CYC1}$) | |
| MaFAR7 | 403 | WRY1 (208a::P$_{TEF1}$-MaFAR7-T$_{CYC1}$) | |
| TaFAR1 | 404 | WRY1 (208a::P$_{TEF1}$-TaFAR1-T$_{CYC1}$) | |
| MmFAR1 | 405 | WRY1 (208a::P$_{TEF1}$-MmFAR1-T$_{CYC1}$) | |
| FAR | 406 | yL405 (1622b::P$_{GAL1}$-MmFAR1-T$_{TDH1}$) | |
| FAR-GFP | 407 | yL405 (1622b::P$_{GAL1}$-MmFAR1-GFP-T$_{TDH1}$) | |
| MBP-FAR | 408 | yL405 (1622b::P$_{GAL1}$-MBP-MmFAR1-T$_{TDH1}$) | |
| MBP-FAR-GFP | 409 | yL405 (1622b::P$_{GAL1}$-MBP-MmFAR1-GFP-T$_{TDH1}$) | |
| ACC1** | 410 | yL405 (YPRCd15c::P$_{GAL1}$-ACC1**-T$_{ENO2}$) | |
| HFA1cyt | 411 | yL405 (YPRCd15c::P$_{GAL1}$-HFA1cyt-T$_{ENO2}$) | |
| dga1Δ | 412 | yL404 (dga1Δ) | |
| lro1Δ | 413 | yL404 (lro1Δ) | |
| are2Δ | 414 | yL404 (are2Δ) | |
| are1Δ | 415 | yL404 (are1Δ) | |
| pxa1Δ | 416 | yL404 (pxa1Δ) | |
| pox1Δ | 417 | yL404 (pox1Δ) | |
| hfd1Δ | 418 | yL404 (hfd1Δ) | |
| adh6Δ | 419 | yL404 (adh6Δ) | |
| tdh3Δ::BcGapN | 420 | yL404 (tdh3Δ::BcGapN) | |
| tdh3Δ::KlGapDH | 421 | yL404 (tdh3Δ::KlGapDH) | |
| pgi1Δ::ZWF1 | 422 | yL404 (pgi1Δ::ZWF1) | |
| gdh1Δ | 423 | yL404 (gdh1Δ) | |
| OLE1 | 424 | yL405 (1014a::P$_{TEF2}$-OLE1-T$_{ADH1}$) | |
| opi1Δ::INO2 | 425 | yL405 (opi1Δ::P$_{TPI1}$-INO2-T$_{PGK1}$) | |
| rpd3Δ | 426 | yL405 (rpd3Δ) | |
| 2RA | 427 | yL406 (YPRCd15c::P$_{GAL1}$-ACC1**-T$_{ENO2}$) | |
| 2RAh | 428 | yL427 (hfd1Δ) | |
| 2RAha | 429 | yL427 (hfd1Δ, adh6Δ) | |
| 2RAhag | 430 | yL427 (hfd1Δ, adh6Δ, gdh1Δ) | |
| 3RAhag | 431 | yL430 (1114a::P$_{GAL1}$-MmFAR1-T$_{TDH1}$) | |

TABLE 1-continued

Strains. The following strains are available from the
JBEI registry (webpage for: public-registry.jbei.org)

| Strain | yL# | Parent (additional genetic changes) | Reference |
|---|---|---|---|
| 2RAhagd | 432 | yL430 (dga1Δ) | |
| 2RAhagdO | 433 | yL430 (dga1Δ, 1014a::$P_{TEF2}$-OLE1-$T_{ADH1}$) | |
| 2RAhagdOG | 434 | yL433 (gal80Δ::$P_{TDH3}$-GAL4) | |

Pull: Comparing fatty acyl-CoA reductase variants

Figure 2A:
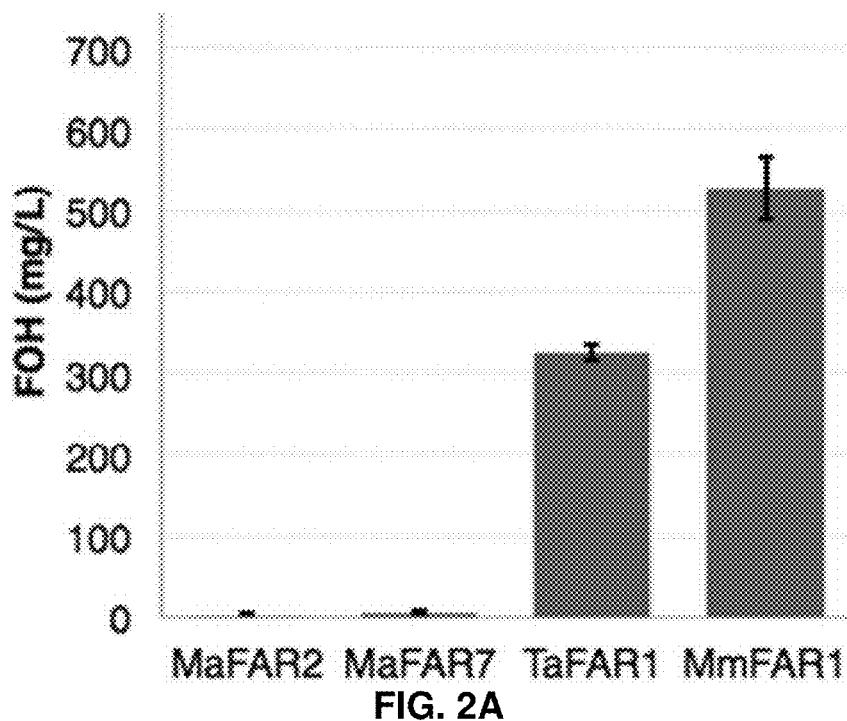
FIG. 2A. Comparing four heterologous fatty acid reductases in *S. cerevisiae*. Four FARs are chromosomally integrated into a fatty acyl-CoA overproducing strain (WRY1) and fatty alcohol production by the resulting strains is compared. Abbrev.: MaFAR2, Maqu2220 from *Marinobacter aquaeoli*; MaFAR7, Maqu2507 from the same organism; TaFAR1, FAR1 from *Tyto alba*; MmFAR1, FAR1 from *Mus musculus*. All four FARs are expressed from the same 208a locus, TEF1 promoter, and CYC1 terminator. Cultures are grown in 5 ml YPD overlaid with 10% dodecane for three days. The bars represent the mean, and the error bars one standard deviation, for three to four biological replicates.
Figure 2B:
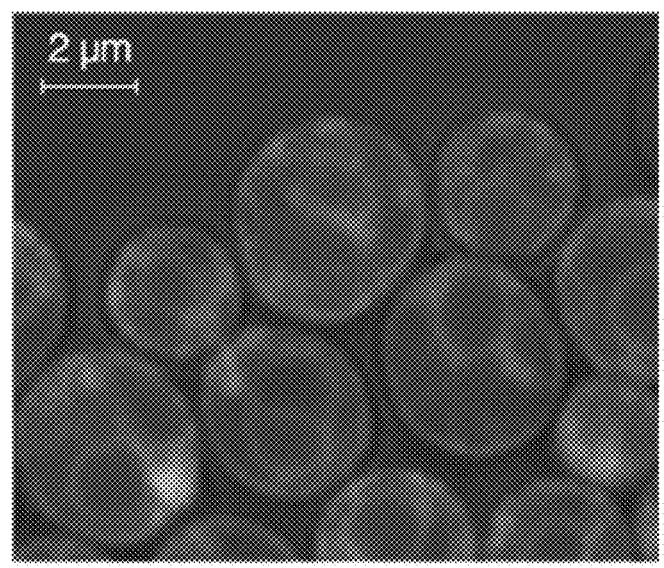
FIG. 2B. Comparing four heterologous fatty acid reductases in *S. cerevisiae*. Confocal microscopy images of yL405 containing MmFAR-GFP shows the fusion enzyme to be ER-localized, as are many native enzymes that use the same substrate fatty acyl-CoA (Natter et al., 2005).

To pull flux towards the product, first the only heterologous enzyme in the pathway is focused, fatty acid reductase (FAR), which converts fatty acyl-CoA produced by fatty acid biosynthesis into fatty alcohols. Besides an earlier report expressing a Mus musculus FAR in S. cerevisiae (Runguphan and Keasling, 2013), other labs have reported on heterologously expressing a FAR from Tyto alba (Feng et al., 2015) and two from Marinobacter hydrocarbonasticus (Liu et al., 2013; Wahlen et al., 2009; Willis et al., 2011). To determine the variant most effective for fatty alcohol production in S. cerevisiae, the four FAR coding sequences (MmFAR1, TaFAR1, MaFAR2, and MaFAR7 are codon-optimized for S. cerevisae) are chromosomally integrated individually into the fatty acyl-CoA-overproducing strain WRY1, and compared fatty alcohol production using GC-MS (FIGS. 2A and 2B). Of the four enzymes, MmFAR1 led to the highest titer at ~550 mg/L (mass of extracted fatty alcohols/aqueous culture volume). TaFAR1 produced two thirds of that, and the two Marinobacter FARs negligible levels. MmFAR1 produced mostly C16 fatty alcohols (87% C16, 7% C18, and 3% each C12 and C14), similar to the distribution from TaFAR1. The strain containing the best-performing MmFAR1 gene (208a::$P_{TEF1}$-FAR, acc1::$P_{TEF1}$-ACC1, fas1::$P_{TEF1}$-FAS1, fas2::$P_{TEF1}$::FAS2) is the base strain for all subsequent engineering and is henceforth referred to as yL405.

Figure 3A:
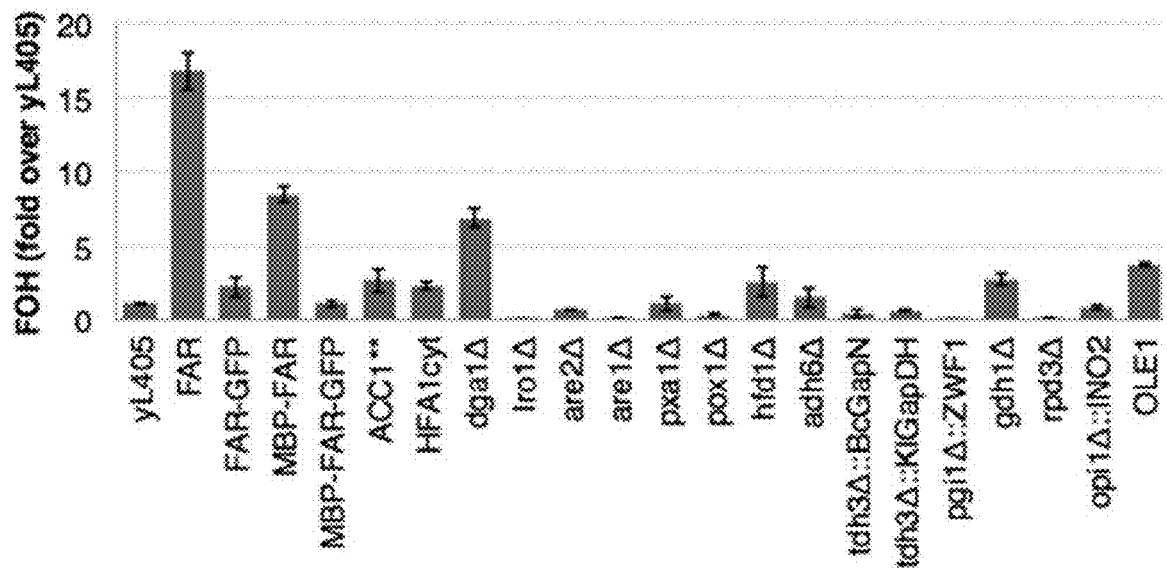
FIG. 3A. Genetic modifications to improve fatty alcohol production. Genetic modifications to yL405 (an acyl-CoA overproducing strain containing one copy of the best-performing MmFAR) are screened in parallel for improvements to fatty alcohol production, with titer shown as a fraction of the parent yL405. Culture is grown in plastic 24-well plates containing 1 ml YPG overlaid with 20% dodecane for three days. The bars represent the mean, and the error bars one standard deviation, for three to four biological replicates.

Having determined MmFAR1 to be the best enzyme candidate for fatty alcohol production, next it is overexpressed further to investigate whether this reaction still limited production. Starting with yL405, a second MmFAR is added—in a cassette containing the strongest promoter (from GAL1) and terminator (from TDH1) reported in recent studies (Lee et al., 2015; Reider Apel et al., 2016)—which increased fatty alcohol titer by 16 fold (FIG. 3A). In parallel, yL405 a version of the second MmFAR fused at the C-terminus to a green fluorescent protein (GFP) is added to examine enzyme solubility and localization. Confocal microscopy showed GFP localization in a pattern typical of the endoplasmic reticulum (ER) common in lipid metabolic enzymes (Natter et al., 2005) (FIG. 2B). This localization is not found to be problematic since many yeast enzymes that utilize fatty acyl-CoA as substrate (e.g., fatty acyl-CoA elongase Elo1p; desaturase Ole1p; acyl-CoA:sterol acyl-transferases Are2p and Are1p) localize to the ER; and since MmFar1p produced high levels of fatty alcohols. However, since fatty acyl-CoA is produced in the cytoplasm, it is wondered whether a soluble, cytoplasmic MmFar1p might access additional substrate and further increase titer. Since MmFar1p fused C-terminally to GFP maintained membrane localization, it is hypothesized that the N-terminus might contain a membrane-targeting signal and that adding an N-terminal maltose binding protein (MBP) might result in a soluble fusion protein. Either MBP-FAR or MBP-FAR-GFP (to verify localization) is introduced to yL405. However, the strain containing MBP-FAR-GFP did not show cytosolic GFP localization, and none of the fusion enzymes improved fatty alcohol production over an untagged second copy of MmFAR (FIG. 3A).

Push: Overexpressing Acetyl-CoA Carboxylase Variants

To push flux through potential bottlenecks, the first committed—and limiting (Tehlivets et al., 2007)—step of fatty acid biosynthesis is focused upon: the production of malonyl-CoA by acetyl-CoA carboxylase (ACC), in yeast encoded by ACC1. Although in an earlier work a strong promoter to drive ACC1 is introduced, the present shotgun proteomics analysis detected much lower levels of Acc1p compared to Fas1p and Fas2p expressed from the same TEF1 promoter. It is known that the gene product of ACC1 is regulated post-transcriptionally, e.g., through phosphorylation sites that inhibit ACC1 activity. Recent work has shown that mutating two serine residues on Acc1p (S659A, S1157A) can produce high levels of malonyl-CoA-derived products (Shi et al., 2014). Therefore yL405 is introduced into a second copy of ACC1 containing these two mutations (ACC1) expressed from the strong GAL1 promoter. In parallel, a cytosolic version of S. cerevisiae's native mitochondrial ACC is constructed, HFA1, by replacing the latter's N-terminal mitochondrial targeting signal with the ACC1 N-terminus (HFA1cyt). This fusion protein has been shown to rescue an acc1Δ phenotype (Hoja et al., 2004) and does not contain any Snf1p target sites, or presumably any other uncharacterized or indirect inactivation mechanisms since Hfa1p activity is required for proliferating mitochondria during respiration when Snf1p signaling is active. Both ACC proteins improved fatty alcohol production compared to yL405, with ACC1 leading to the best improvement at 2.6 fold.

Block: Inhibiting Reactions Fatty Alcohols and Intermediates

To block undesirable reactions, eight genes encoding enzymes that consume fatty acyl-CoA or fatty alcohols are deleted. These included enzymes that produce triacylglycerides (TAGs) for storage (DGA1 and LRO1) or steryl esters (ARE2 and ARE1), the peroxisomal importer (PXA1), the first step of beta-oxidation (POX1), and two that dehydrogenate fatty alcohols (HFD1 and ADH6). These deletions in parallel on the base strain yL405 are performed and screened for fatty alcohol production. Of the resulting eight deletion strains, dga1Δ had the highest titer (at 6.8-fold higher than parent yL405 strain), followed by hfd1Δ (at 2.6-fold higher), then adh6Δ (at 1.5-fold higher). None of the other deletions led to any improvement in titer.

Optimizing NADPH/NADP+ and NADH/NAD+ Cofactor Usage

Besides pull-push-block engineering of carbon flux, balancing redox cofactor usage is focused upon. As discussed above, the fatty alcohol pathway produces excess NADH and requires additional NADPH. To remediate this redox cofactor imbalance in the fatty alcohol pathway, first replacing native NADH-producing GapDH with an NADPH-producing variant as has been pursued for other bioproducts is considered (Guo et al., 2011; Kildegaard et al., 2016; Zhang et al., 2011). From the proteomics results, it is found that of the three GapDH isoenzymes in yeast, Tdh3p is the most highly expressed. Thus TDH3 is replaced with either an NADPH-producing GapDH from *Kluyveromyces lactis* (KlGapDH) (Verho et al., 2002), or a non-phosphorylating GapDH from *Bacillus cereus* (BcGapN) (Guo et al., 2011) in the baseline yL405 strain. Neither resulting strain produced more fatty alcohols than the parent (FIG. 3A). It is noted that the reaction catalyzed by GapDH has a positive $\Delta G^0 = 1.5$ kcal/mol (Stryer, 1988). Normally, a chemical driving force afforded by a high cellular [NAD$^+$]/[NADH] ratio makes the concentration-adjusted $\Delta G$ spontaneous. For an NADP$^+$-dependent reaction, however, the cofactor ratio is inverted ([NADP$^+$]/[NADPH]<1) suggesting such a reaction might result in a bottleneck, or futile cycling between a forward, NADH-generating flux catabolized by the remaining native Tdh1p and Tdh2p, and a reverse, NADPH-consuming flux catabolized by KlGapdhp. The reaction catalyzed by BcGapnp, on the other hand, has a very favorable $\Delta G^0$, but skips the ATP-generating step that normally follows GapDH, thus creating a pathway ATP deficit. Similar thermodynamic considerations stemming from concentration gradients across the redox cofactor pairs are relevant to other pathways.

Next, it is sought to increase NADPH availability for fatty acid biosynthesis. This flux reconstruction indicated that the fatty acid pathway consumes only ~5% of cellular ATP, but 40% of cellular NADPH, suggesting the latter cofactor may limit production. The quantitative analysis further showed that (1) carbon flux through the NADPH-producing pentose phosphate pathway is only 2% of that through PGI1, (2) Pgi1p is expressed highly, and (3) Zwf1p—the first and limiting enzyme of the pentose phosphate—is undetectable even though downstream pentose phosphate enzymes are detected. Thus, it is attempted to force flux through the pentose phosphate pathway by deleting PGI1 and in its place overexpressing ZWF1 (pgi1Δ::ZWF1), also in the yL405 strain. However, the resulting strain grew slowly and barely produced any fatty alcohols (FIG. 3A).

Lastly, it is attempted to minimize NADPH consumed by competing reactions. This flux analysis indicated that 60% of all NADPH is consumed to produce glutamate (from alpha-ketoglutarate and ammonia) with the two isoenzymes catabolizing this reaction, Gdh1p and Gdh3p, expressed at 0.12% and 0.034% of soluble protein, respectively. It is theorized that deleting GDH1 might slow down glutamate biosynthesis and free up NADPH for fatty acid biosynthesis, as well as carbon. It is thus introduced a gdh1Δ deletion into yL405, resulting in a 2.7-fold improvement in fatty alcohol production.

Perturbations to Fatty Acid Regulation

The fatty acid pathway is energy intensive and regulated at several levels (Tehlivets et al., 2007). Some of the strategies address known levels of regulation—e.g., using a strong constitutive promoter to overexpress ACC1, FAS1, and FAS2; or abolishing post-translational phosphorylation sites on ACC1—yet additional known or unknown regulatory mechanisms may continue to limit pathway flux. A recent study showed that deleting a histone deacetylase encoded by RPD3 dramatically increased fatty alcohol production from an *S. cerevisiae* strain expressing TaFAR (Feng et al., 2015). In yL405, rpd3Δ did not yield any improvement (FIG. 3A). The gene encoding the negative regulator of fatty acid biosynthesis, OPI1, is also deleted and in its place overexpressed the positive regulator encoded by INO2 in yL405. However, the opi1Δ::INO2 replacement does not improve fatty alcohol titers (FIG. 3A).

Lastly, a report found that (1) a correlation in mammalian tissues between lipid accumulation (as TAGs) and expression level of Δ9-desaturase (which produces mono-unsaturated fatty acyl-CoA), and (2) that overexpression of Δ9-desaturase *Yarrowia lipolitica* led to dramatically increased levels of TAGs in an engineered strain (Qiao et al., 2015). To explore the possibility of Δ9-desaturase increasing flux through the fatty alcohol pathway in *S. cerevisiae*—by increasing membrane fluidity and access of MmFar1p to substrate (Degreif et al., 2017), or through an indirect feedback inhibition as in other organisms (Zhang et al., 2012)—the native *S. cerevisiae* Δ9-desaturase (encoded by OLE1) in yL405 is overexpressed, resulting in a 4-fold improvement in fatty alcohol titer (FIG. 3A).

Combining Beneficial Genetic Edits into Highest-Producing Strain

Figure 3B:
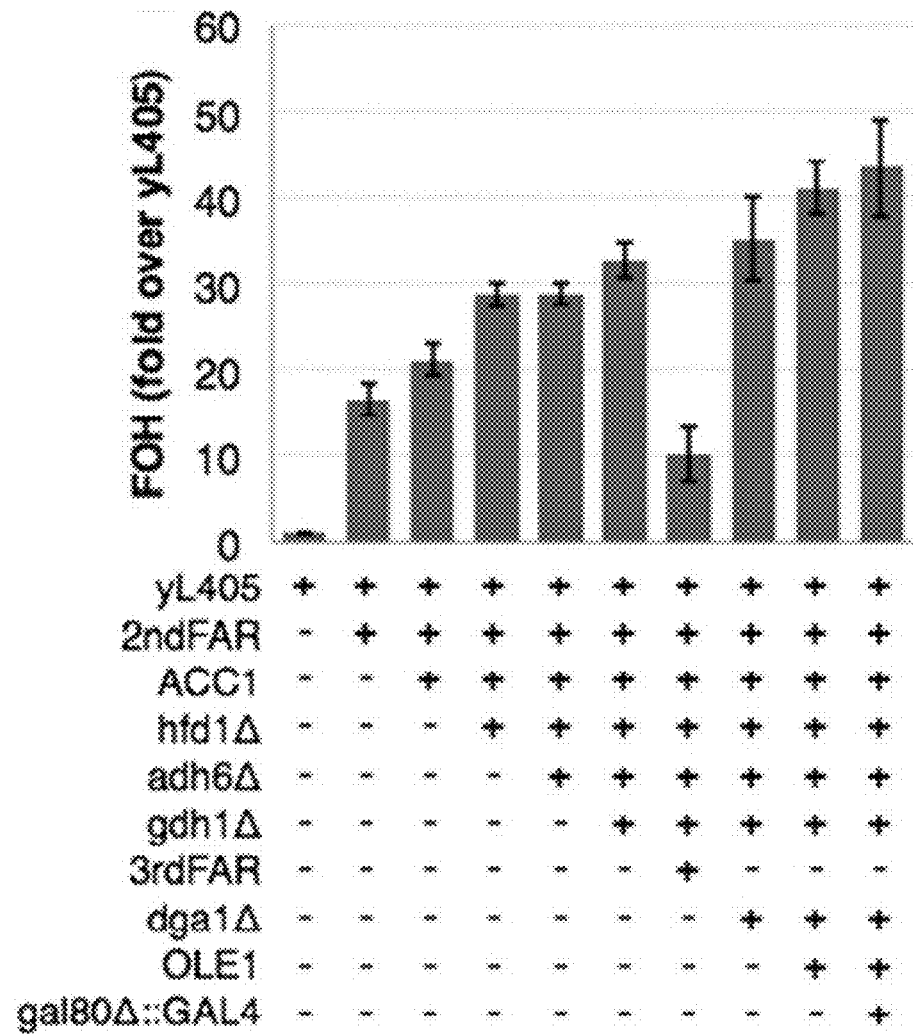
FIG. 3B. Genetic modifications to improve fatty alcohol production. Stacking beneficial single-gene edits leads to additional improvements in titer culminating in the highest producing strain yL434. Culture is grown in plastic 24-well plates containing 1 ml YPG overlaid with 20% dodecane for three days. The bars represent the mean, and the error bars one standard deviation, for three to four biological replicates.

Having found several genetic modifications that improved fatty alcohol titers, beneficial changes into a high-producing strain are next stacked. Starting with the best single-edit strain containing a second copy of FAR, then ACC1** is added, resulting in an additional 4.6-fold improvement over yL405 (FIG. 3B). Then deletions of hfd1Δ, adh6Δ, and gdh1Δ are stacked, increasing titer up to 32.7-fold above yL405. Because a second copy of FAR led to the most dramatic improvement in titer in the single-gene edit strains, a third copy is added to examine whether FAR activity remained limiting, but found the resulting strain produced less than parent (FIG. 3B). Instead, the remaining beneficial single-gene edits dga1Δ and OLE1 are combined to reach a titer 40-fold higher than yL405.

Figure 3C:
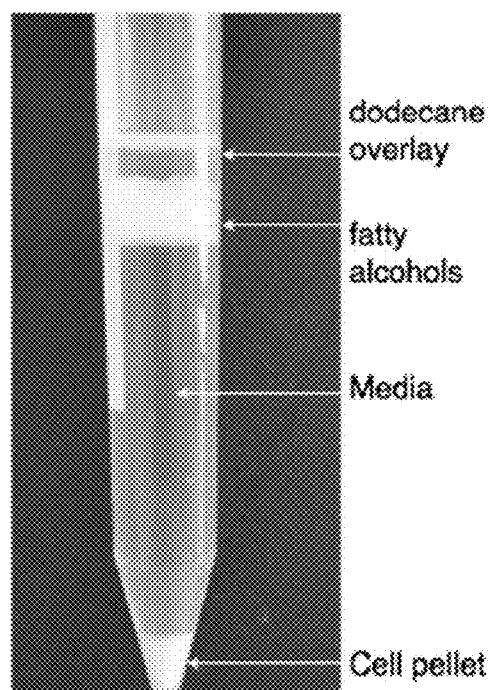
FIG. 3C. Genetic modifications to improve fatty alcohol production. The high production level from yL434 results in precipitation of fatty alcohols from the saturated dodecane overlay. The culture is grown in a 250-ml baffled flask containing 10 ml YPD overlaid with 20% dodecane for three days.

Lastly, it is sought to deregulate the GAL1 promoter driving MmFAR and ACC1 by deleting the negative regulator of galactose metabolism (GAL80) and in its place introducing a copy of the positive regulator (GAL4). This perturbation in galactose metabolism has the advantage of making the GAL1 promoter constitutively active in glucose, allowing us to achieve high production using this inexpensive sugar as the carbon source. The final yL427 strain, containing two copies of MmFAR, ACC1, deletions of dga1Δ, hfd1Δ, adh6Δ, and gdh1Δ, overexpression of OLE1, and a gal80Δ::GAL4 replacement produced 43-fold more fatty alcohols than the original yL405 strain (FIG. 3B). At this level of production, precipitation of fatty alcohols from the saturated dodecane overlay in yL434 cultures is observed (FIG. 3C).

Fatty Alcohol Production from Biomass Sugars Released Using Renewable Ionic Liquid.

Having demonstrated a high-producing strain, then production from lignocellulosic feedstocks derived from non-food bioenergy crops is evaluated. Specific combinations of anions and cations that are liquids at room temperature (termed "ionic liquids", ILs) have been shown to deconstruct plant biomass, allowing for subsequent enzymatic de-polymerization to free constituent sugars (Zhu et al., 2006). However, these processes are limited by high costs of conventional ILs, water usage, and toxicity. Recently, attention has shifted to ILs derived from benign cholinium cations stabilized with readily available bio-based anions (Petkovic et al., 2010; Sun et al., 2016). A recently demonstrated one-pot process involving biomass pretreatment with ILs composed of cholinium and amino acids followed by enzymatic saccharification requires minimal water and unit operations, thus dramatically lowering process costs (Xu et al., 2016).

Figure 4A:
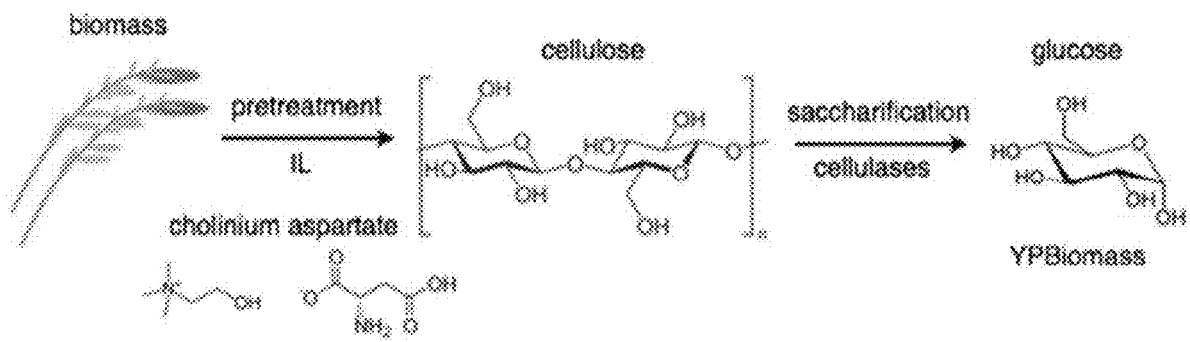
FIG. 4A. Fatty alcohol production from lignocellulosic biomass. Biomass pretreatment with ionic liquids (ILs) containing cholinium cation paired with bio-based anions, e.g., aspartate, break down lignocellulose to be depolymerized using cellulase enzymes to free constituent sugars.
Figure 4B:
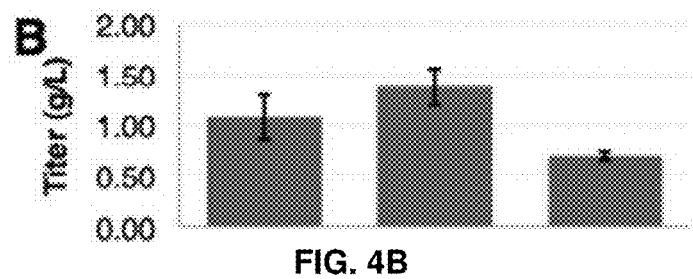
FIG. 4B. Fatty alcohol production from lignocellulosic biomass. The highest producing yL434 strain grown in biomass hydrolysates media (YPBiomass) or conventional rich (YPD or YPG) media produces high levels of fatty alcohols. Cultures are grown in plastic 250-ml baffled flasks containing 10 ml medium overlaid with 20% dodecane for three days. The bars represent the mean, and the error bars one standard deviation, for three replicates.
Figure 4C:
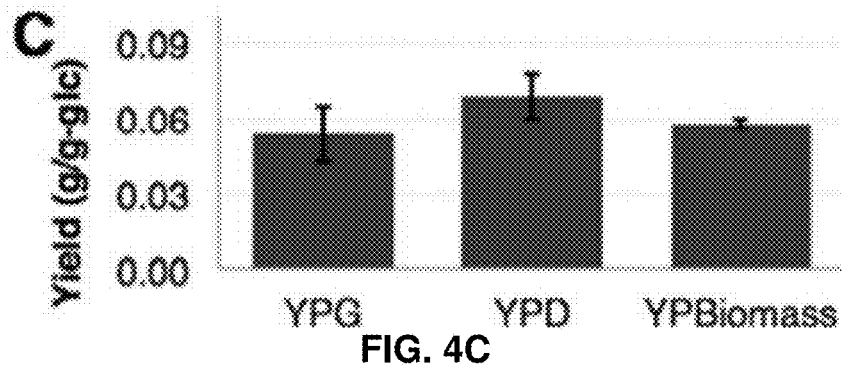
FIG. 4C. Fatty alcohol production from lignocellulosic biomass. The highest producing yL434 strain grown in biomass hydrolysates media (YPBiomass) or conventional rich (YPD or YPG) media produces high yields of fatty alcohols. Cultures are grown in plastic 250-ml baffled flasks containing 10 ml medium overlaid with 20% dodecane for three days. The bars represent the mean, and the error bars one standard deviation, for three replicates.
Figure 5A:
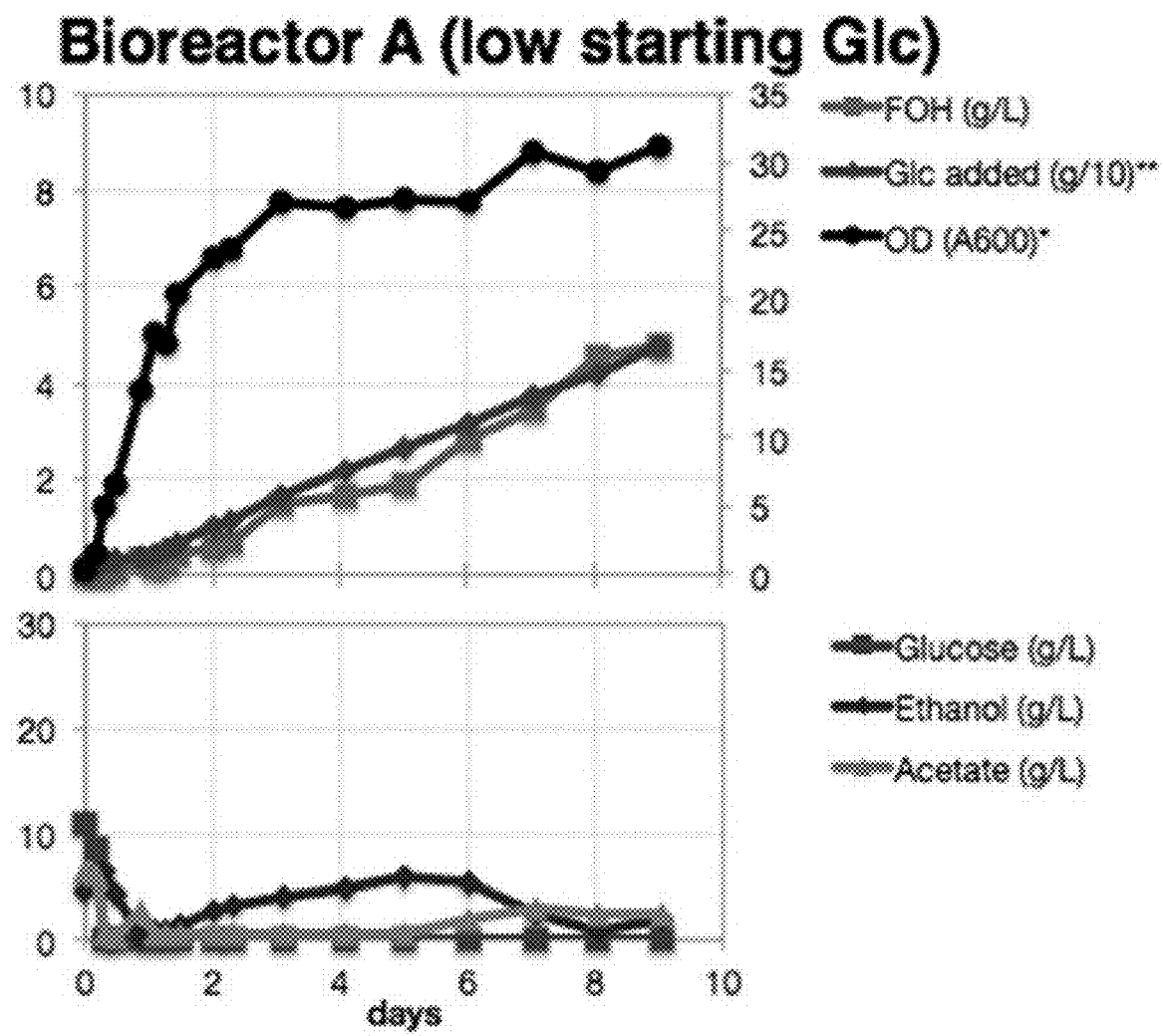
FIG. 5A. High-density, fed-batch bioreactor fermentations. The highest producing yL434 strain is grown in 2 L-scale bioreactors under different fed-batch conditions to maximize titer. Bioreactor A contained half the normal glucose concentration in batch phase (1% vs. 2% for others) and is fed a constant ~1.5 g/hr concentrated glucose.
Figure 5B:
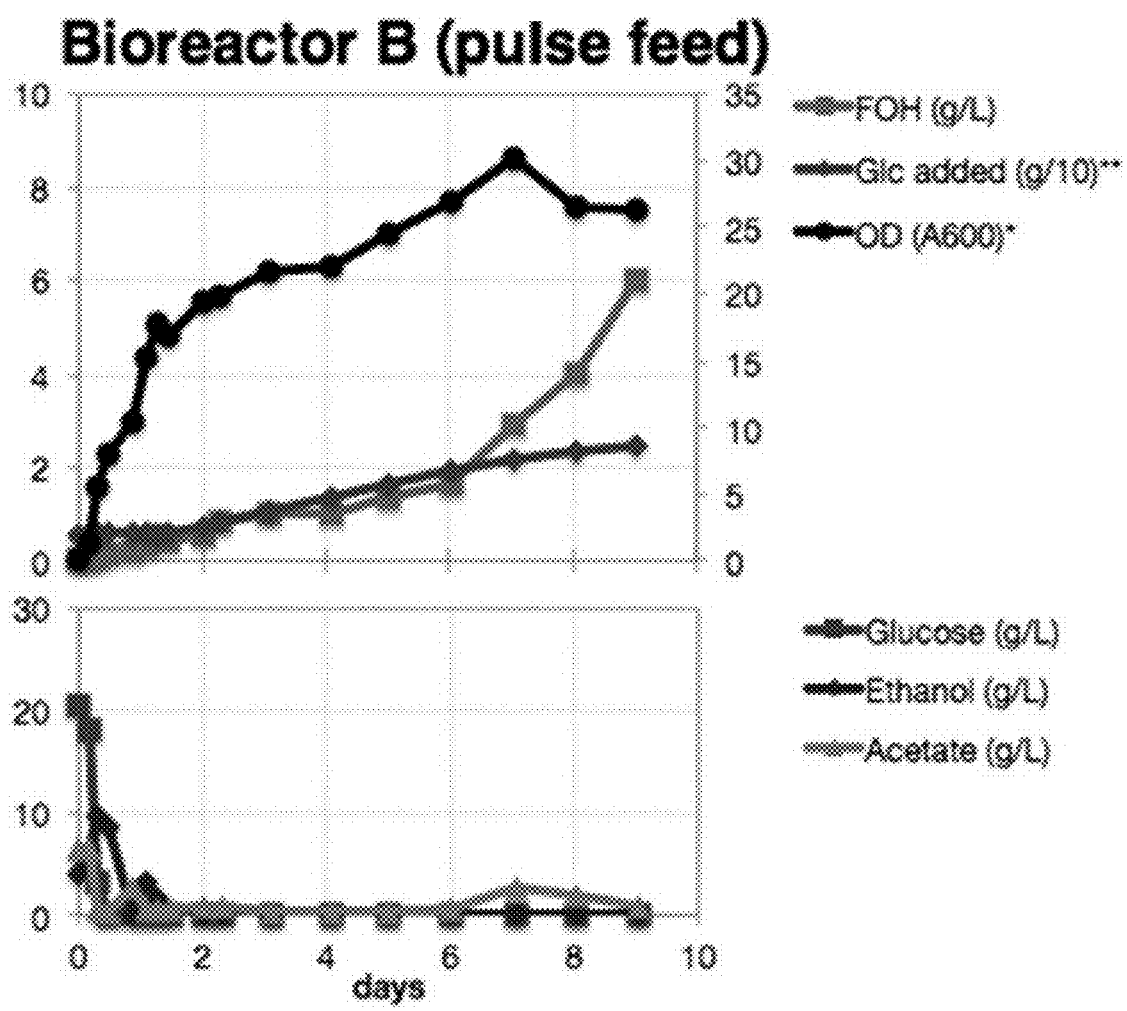
FIG. 5B. High-density, fed-batch bioreactor fermentations. The highest producing yL434 strain is grown in 2 L-scale bioreactors under different fed-batch conditions to maximize titer. Bioreactor B is pulse-fed ~1 g/hr (1 g pulses of concentrated glucose upon carbon source depletion as indicated by $O_2$ spike, occurring every ~1 hr).
Figure 5C:
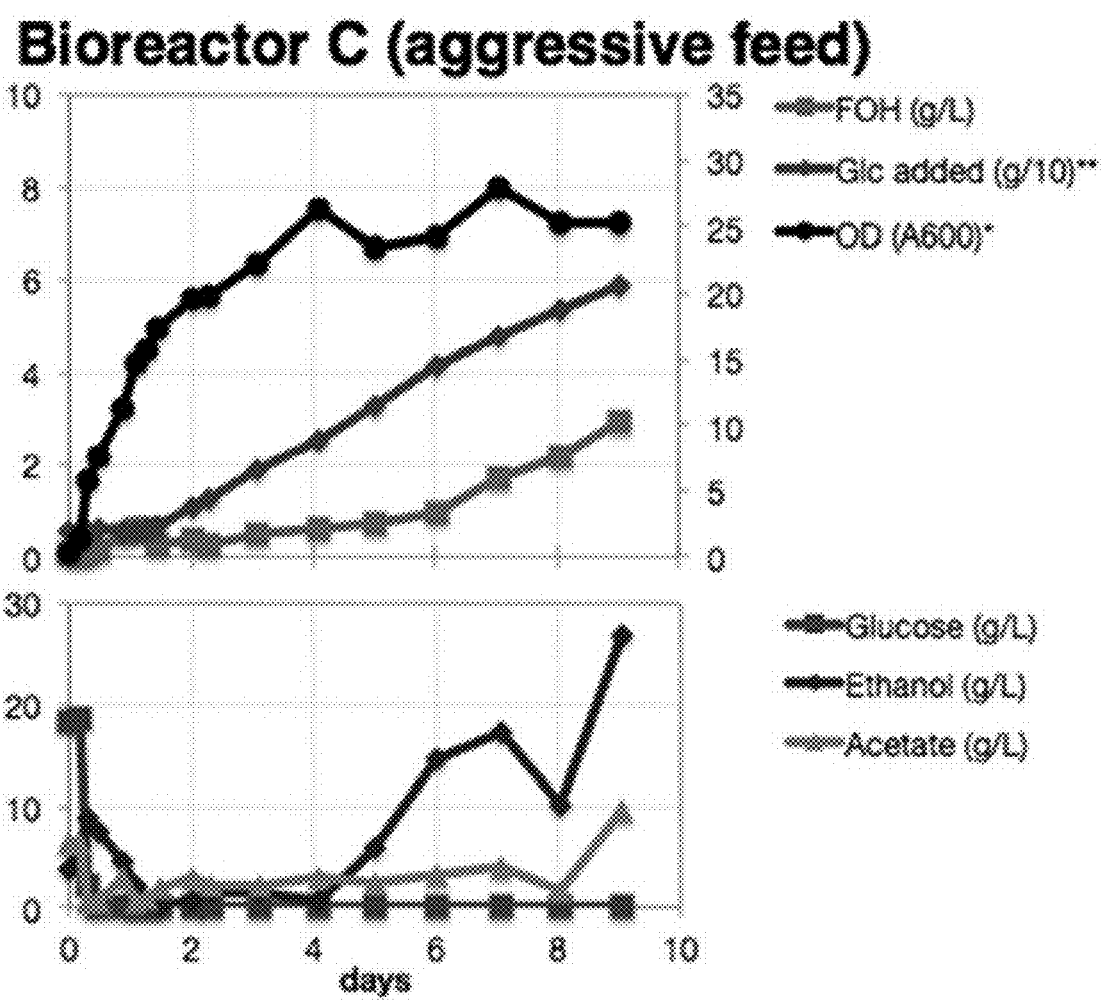
FIG. 5C. High-density, fed-batch bioreactor fermentations. The highest producing yL434 strain is grown in 2 L-scale bioreactors under different fed-batch conditions to maximize titer. Bioreactor C is fed a constant ~3 g/hr.
Figure 5D:
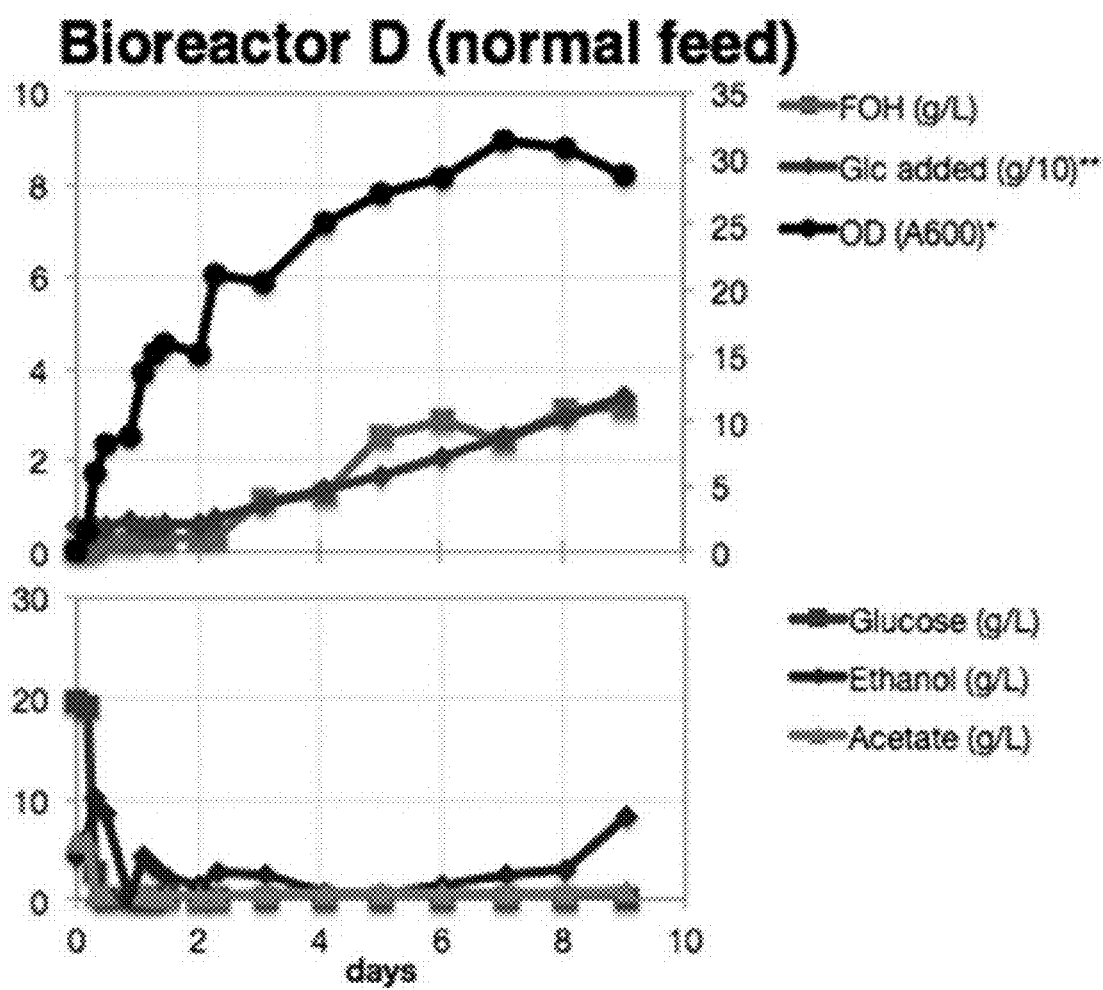
FIG. 5D. High-density, fed-batch bioreactor fermentations. The highest producing yL434 strain is grown in 2 L-scale bioreactors under different fed-batch conditions to maximize titer. Bioreactor D is fed a constant ~1.5 g/hr.

To examine the feasibility of using lignocellulosic feedstocks to produce fatty alcohols, two types of non-food crops are pretreated (switchgrass and *Sorghum*) with cholinium-based ILs containing three common bio-based anions (lysinate, alpha-ketoglutarate, or aspartate) in a one-pot process (see Materials and Methods). The six resulting biomass hydrolysate media all contained ~1% glucose, and all produced more than 150 mg/L fatty alcohols using the baseline strain yL405. The biomass hydrolysates media derived from *Sorghum* pretreated with cholinium aspartate produced the most at 400 mg/L, fatty alcohols, and is further referred to as YPBiomass. Then the highest producing yL434 strain in YPBiomass is grown (as well as traditional rich media YPD and YPG) in baffled flasks, finding in preliminary experiments that greater aeration lead to improved production. Fatty alcohol levels reached 0.7 g/L in YPBiomass, corresponding to ~0.06 g/g-glucose, already above the highest reported titers and yields (in shake flasks) using any media (Zhou et al., 2016). In YPD medium, fatty alcohol production reached 1.2 g/L and 0.07 g/g-glucose (FIGS. 4A to 4C), corresponding to ~20% of the maximum theoretical yield, well above all previous reports of fatty alcohol production in *S. cerevisiae*.

Fed-Batch Bioreactor Fermentations

Finally, maximizing titer and demonstrating scale-up are realized in fed-batch fermentation. Previous work on *S. cerevisiae* has suggested maximal yields depend on a balance between feeding enough sugar to maintain high product flux, but not too much as to induce overflow metabolism (Mazzoleni et al., 2015). To that end, 2-L scale bioreactors are set up with feed strategies aimed at minimizing overflow metabolism and maximizing titer. For all four bioreactors, yL434 is cultured in an initial 1-L YPD in batch operation until glucose depletion (as indicated by $O_2$ spike), and then added concentrated glucose following different feed strategies: bioreactor A contained half the normal glucose concentration in batch phase (1% vs. 2% for others) and is fed a constant ~1.5 g/hr concentrated glucose; bioreactor B is pulse-fed ~1 g/hr (as ~1 g pulses of concentrated glucose upon carbon source depletion as indicated by $O_2$ spike, occurring every ~1 hr); bioreactor C a constant ~3 g/hr; and bioreactor D a constant ~1.5 g/hr. All four bioreactors reached ODs of 25-31 and fatty alcohol titers >3 g/L and are still climbing at the end of the allotted 9-day fermentation time (FIGS. 5A to 6D). Bioreactor A showed the greatest rate of fatty alcohol production in fed-batch phase, the highest final titer, and the lowest feed consumption, with the overlay showing extensive precipitation of fatty alcohols. The final titer is 6 g/L, and the yield 58 mg/g-glucose, corresponding to 17% of the maximum theoretical yield.

CONCLUSIONS

In this work, *S. cerevisiae* is engineered for high-level production of fatty alcohols guided by quantitative analysis of global protein expression and flux modeling. Four heterologous fatty acid reductases are compared, finding high activity and ER localization from a *Mus musculus* FAR. After screening an additional 21 single-gene edits, the following successful strategies to improve titer are identified: (1) increasing expression of MmFAR1, (2) deleting competing reactions encoded by DGA1, HFD1, and ADH6, (3) overexpressing a mutant of the bottleneck enzyme encoded by ACC1 insensitive to post-transcriptional and post-translational repression, (4) limiting NADPH and carbon flux to glutamate biosynthesis by deleting the enzyme encoded by GDH1, and (5) limiting fatty acid pathway repression by overexpressing the desaturase encoded by OLE1. The final strain containing eleven genetic modifications compared to the parent BY4741 strain produced 1.2 g/L fatty alcohols in shake flasks.

High-level production from feedstocks produced from non-food crops and cholinium-based renewable bionic ILs is also demonstrated, reaching a titer of 0.7 g/L in shake flasks. Lastly, scale-up fermentation and explored alternative feeding strategies aimed at limiting overflow metabolism is demonstrated, achieving a titer of 6.0 g/L in a 2-L, fed-batch bioreactor. These titers are the highest for fatty alcohols reported to date for *S. cerevisiae*. To our knowledge, this is also the first report of a bioproduct produced by yeast from feedstocks derived solely from biomass.

References cited are:

Batth, T. S., Keasling, J. D., Petzold, C. J., 2012. Targeted Proteomics for Metabolic Pathway Optimization, in: Fungal Secondary Metabolism: Methods and Protocols, Methods in Molecular Biology, Vol. 944. pp. 47-58. doi:10.1007/978-1-62703-122-6

Brachmann, C. B., Davies, A., Cost, G. J., Caputo, E., Li, J., Hieter, P., Boeke, J. D., 1998. Designer deletion strains derived from *Saccharomyces cerevisiae* S288C: A useful set of strains and plasmids for PCR-mediated gene disruption and other applications. Yeast 14, 115-132. doi: 10.1002/(SICI)1097-0061(19980130)14:2<115::AID-YEA204>3.0.CO; 2-2

Caspeta, L., Nielsen, J., 2013. Economic and environmental impacts of microbial biodiesel. Nat. Biotechnol. 31, 789-93. doi:10.1038/nbt.2683

Clomburg, J. M., Blankschien, M. D., Vick, J. E., Chou, A., Kim, S., Gonzalez, R., 2015. Integrated engineering of β-oxidation reversal and ω-oxidation pathways for the synthesis of medium chain ω-functionalized carboxylic acids. Metab. Eng. 28, 202-212. doi:10.1016/j.ymben.2015.01.007

Connor, R., Uhlenbrook, S., 2016. The United Nations World Water Development Report 2016. Paris, France.

Degreif, D., de Rond, T., Bertl, A., Keasling, J. D., Budin, I., 2017. Lipid engineering reveals regulatory roles for membrane fluidity in yeast flocculation and oxygen-limited growth. Metab. Eng. 41, 46-56. doi:10.1016/j.ymben.2017.03.002

Feng, X., Lian, J., Zhao, H., 2015. Metabolic engineering of *Saccharomyces cerevisiae* to improve 1-hexadecanol production. Metab. Eng. 27, 10-19. doi:10.1016/j.ymben.2014.10.001

Gaikwad, S., 2016. Fatty Alcohol Market Size, Industry Analysis Report: Forecast, 2016-2023. Ocean View, Del.

García Martín, H., Kumar, V. S., Weaver, D., Ghosh, A., Chubukov, V., Mukhopadhyay, A., Arkin, A., Keasling, J. D., 2015. A Method to Constrain Genome-Scale Models with 13C Labeling Data. PLOS Comput. Biol. 11, e1004363. doi:10.1371/journal.pcbi.1004363

Ghosh, A., Ando, D., Gin, J., Runguphan, W., Denby, C., Wang, G., Baidoo, E. E. K., Shymansky, C., Keasling, J. D., García Martín, H., 2016. (13)C Metabolic Flux Analysis for Systematic Metabolic Engineering of *S. cerevisiae* for Overproduction of Fatty Acids. Front. Bioeng. Biotechnol. 4, 76. doi:10.3389/fbioe.2016.00076

Gietz, R. D., Woods, R. a, 2002. Transformation of yeast by lithium acetate/single-stranded carrier DNA/polyethylene glycol method. Methods Enzymol. 350, 87-96.

Goh, E.-B., Baidoo, E. E. K., Keasling, J. D., Beller, H. R., 2012. Engineering of bacterial methyl ketone synthesis for biofuels. Appl. Environ. Microbiol. 78, 70-80. doi: 10.1128/AEM.06785-11

Guo, Z., Zhang, L., Ding, Z., Shi, G., 2011. Minimization of glycerol synthesis in industrial ethanol yeast without influencing its fermentation performance. Metab. Eng. 13, 49-59. doi:10.1016/j.ymben.2010.11.003

Haushalter, R. W., Kim, W., Chavkin, T. A., The, L., Garber, M. E., Nhan, M., Adams, P. D., Petzold, C. J., Katz, L., Keasling, J. D., 2014. Production of anteiso-branched fatty acids in *Escherichia coli*; next generation biofuels with improved cold-flow properties. Metab. Eng. 26C, 111-118. doi:10.1016/j.ymben.2014.09.002

Hoja, U., Marthol, S., Hofmann, J., Stegner, S., Schulz, R., Meier, S., Greiner, E., Schweizer, E., 2004. HFA1 encoding an organelle-specific acetyl-CoA carboxylase controls mitochondrial fatty acid synthesis in *Saccharomyces cerevisiae*. J. Biol. Chem. 279, 21779-86. doi:10.1074/jbc.M401071200

Kalscheuer, R., Stölting, T., Steinbüchel, A., 2006. Microdiesel: *Escherichia coli* engineered for fuel production. Microbiology 152, 2529-2536. doi:10.1099/mic.0.29028-0

Kildegaard, K. R., Jensen, N. B., Schneider, K., Czarnotta, E., Ozdemir, E., Klein, T., Maury, J., Ebert, B. E., Christensen, H. B., Chen, Y., Kim, I. K., Herrgard, M. J., Blank, L. M., Forster, J., Nielsen, J., Borodina, I., 2016. Engineering and systems-level analysis of *Saccharomyces cerevisiae* for production of 3-hydroxypropionic acid via malonyl-CoA reductase-dependent pathway. Microb. Cell Fact. 15, 13. doi:10.1186/s12934-016-0451-5

Lee, M. E., DeLoache, W. C., Cervantes, B., Dueber, J. E., 2015. A Highly-characterized Yeast Toolkit for Modular, Multi-part Assembly. ACS Synth. Biol. 150414151809002. doi:10.1021/sb500366v Liu, A., Tan, X., Yao, L., Lu, X., 2013. Fatty alcohol production in engineered *E. coli* expressing *Marinobacter* fatty acyl-CoA reductases. Appl. Microbiol. Biotechnol. 97, 7061-71. doi:10.1007/s00253-013-5027-2

Liu, Y., Chen, S., Chen, J., Zhou, J., Wang, Y., Yang, M., Qi, X., Xing, J., Wang, Q., Ma, Y., 2016. High production of fatty alcohols in *Escherichia coli* with fatty acid starvation. Microb. Cell Fact. 15, 129. doi:10.1186/s12934-016-0524-5

Mazzoleni, S., Landi, C., Cartenì, F., de Alteriis, E., Giannino, F., Paciello, L., Parascandola, P., 2015. A novel process-based model of microbial growth: self-inhibition in *Saccharomyces cerevisiae* aerobic fed-batch cultures. Microb. Cell Fact. 14, 109. doi:10.1186/s12934-015-0295-4

Mo, M. L., Palsson, B.Ø., Herrgård, M. J., 2009. Connecting extracellular metabolomic measurements to intracellular flux states in yeast. BMC Syst. Biol. 3, 37. doi:10.1186/1752-0509-3-37

Montague, T. G., Cruz, J. M., Gagnon, J. A., Church, G. M., Valen, E., 2014. CHOPCHOP: A CRISPR/Cas9 and TALEN web tool for genome editing. Nucleic Acids Res. 42, 401-407. doi:10.1093/nar/gku410

Natter, K., Leitner, P., Faschinger, A., Wolinski, H., McCraith, S., Fields, S., Kohlwein, S. D., 2005. The spatial organization of lipid synthesis in the yeast *Saccharomyces cerevisiae* derived from large scale green fluorescent protein tagging and high resolution microscopy. Mol. Cell. Proteomics 4, 662-72. doi:10.1074/mcp.M400123-MCP200

Petkovic, M., Ferguson, J. L., Gunaratne, H. Q. N., Ferreira, R., Leitão, M. C., Seddon, K. R., Rebelo, L. P. N., Pereira, C. S., Pereira, C. S., Ferreira, R., Seddon, K. R., Rebelo, L. P. N., Pereira, C. S., 2010. Novel biocompatible cholinium-based ionic liquids—toxicity and biodegradability. Green Chem. 12, 643. doi:10.1039/b922247b Pfleger, B. F., Gossing, M., Nielsen, J., 2015. Metabolic engineering strategies for microbial synthesis of oleochemicals. Metab. Eng. 29, 1-11. doi:10.1016/j.ymben.2015.01.009

Qiao, K., Imam Abidi, S. H., Liu, H., Zhang, H., Chakraborty, S., Watson, N., Kumaran Ajikumar, P., Stephanopoulos, G., 2015. Engineering lipid overproduction in the oleaginous yeast *Yarrowia lipolytica*. Metab. Eng. 29, 56-65. doi:10.1016/j.ymben.2015.02.005

Reider Apel, A., D'Espaux, L., Wehrs, M., Sachs, D., Li, R. A., Tong, G. J., Garber, M., Nnadi, O., Zhuang, W., Hillson, N. J., Keasling, J. D., Mukhopadhyay, A., 2016. A Cas9-based toolkit to program gene expression in *Saccharomyces cerevisiae*. Nucleic Acids Res. 1-14. doi:10.1093/gbe/evw245

Runguphan, W., Keasling, J. D., 2013. Metabolic Engineering of *Saccharomyces cerevisiae* for Production of Fatty Acid-Derived Biofuels and Chemicals. Metab. Eng. 21, 103-113. doi:10.1016/j.ymben.2013.07.003

Shi, S., Chen, Y., Siewers, V., 2014. Improving Production of Malonyl Coenzyme A-Derived Metabolites. MBio 5, e01130-14. doi:10.1128/mBio.01130-14.Editor Stryer, L., 1988. Biochemistry. W.H. Freeman.

Sun, J., Konda, N. V. S. N. M., Shi, J., Parthasarathi, R., Dutta, T., Xu, F., Scown, C. D., Simmons, B. A., Singh, S., Andre, B., Arkin, A. P., Astromoff, A., Bakkoury, M. El, Bangham, R., Benito, R., Brachat, S., Campanaro, S., Curtiss, M., Davis, K., Deutschbauer, A., Entian, K. D., Flaherty, P., Foury, F., Garfinkel, D. J., Gerstein, M., Gotte, D., Guldener, U., Hegemann, J. H., Hempel, S., Herman, Z., Jaramillo, D. F., Kelly, D. E., Kelly, S. L., Kotter, P., LaBonte, D., Lamb, D. C., Lan, N., Liang, H., Liao, H., Liu, L., Luo, C. Y., Lussier, M., Mao, R., Menard, P., Ooi, S. L., Revuelta, J. L., Roberts, C. J., Rose, M., Ross-Macdonald, P., Scherens, B., Schimmack, G., Shafer, B., Shoemaker, D. D., Sookhai-Mahadeo, S., Storms, R. K., Strathern, J. N., Valle, G., Voet, M., Volckaert, G., Wang, C. Y., Ward, T. R., Wilhelmy, J., Winzeler, E. A., Yang, Y. H., Yen, G., Youngman, E., Yu, K. X., Bussey, H., Boeke, J. D., Snyder, M., Philippsen, P., Davis, R. W., Johnston, M., 2016. $CO_2$ enabled process integration for the production of cellulosic ethanol using bionic liquids. Energy Environ. Sci. 9, 2822-2834. doi:10.1039/C6EE00913A Tai, M., Stephanopoulos, G., 2013. Engineering the push and pull of lipid biosynthesis in oleaginous yeast *Yarrowia lipolytica* for biofuel production. Metab. Eng. 15, 1-9. doi:10.1016/j.ymben.2012.08.007

Tehlivets, O., Scheuringer, K., Kohlwein, S. D., 2007. Fatty acid synthesis and elongation in yeast. Biochim. Biophys. Acta 1771, 255-70. doi:10.1016/j.bbalip.2006.07.004

Thomas, D., Cherest, H., Surdin-Kerjan, Y., 1991. Identification of the structural gene for glucose-6-phosphate dehydrogenase in yeast. Inactivation leads to a nutritional requirement for organic sulfur. EMBO J. 10, 547-553.

Verho, R., Richard, P., Jonson, P. H., Sundqvist, L., Londesborough, J., Penttilä, M., 2002. Identification of the first fungal NADP-GAPDH from *Kluyveromyces lactis*. Biochemistry 41, 13833-13838. doi:10.1021/bi0265325

Wahlen, B. D., Oswald, W. S., Seefeldt, L. C., Barney, B. M., 2009. Purification, characterization, and potential bacterial wax production role of an NADPH-dependent fatty aldehyde reductase from *Marinobacter aquaeolei* VT8. Appl. Environ. Microbiol. 75, 2758-64. doi:10.1128/AEM.02578-08

Willis, R. M., Wahlen, B. D., Seefeldt, L. C., Barney, B. M., 2011. Characterization of a fatty acyl-CoA reductase from *Marinobacter aquaeolei* VT8: a bacterial enzyme catalyzing the reduction of fatty acyl-CoA to fatty alcohol. Biochemistry 50, 10550-8. doi:10.1021/bi2008646

Xu, F., Sun, J., Konda, N. V. S. N. M., Shi, J., Dutta, T., Scown, C. D., Simmons, B. A., Singh, S., 2016. Transforming biomass conversion with ionic liquids: process intensification and the development of a high-gravity, one-pot process for the production of cellulosic ethanol. Energy Environ. Sci. 9, 1042-1049. doi:10.1039/C5EE02940F Zampar, G. G., Kümmel, A., Ewald, J., Jol, S., Niebel, B., Picotti, P., Aebersold, R., Sauer, U., Zamboni, N., Heinemann, M., 2013. Temporal system-level organization of the switch from glycolytic to gluconeogenic operation in yeast. Mol. Syst. Biol. 9, 651. doi:10.1038/msb.2013.11

Zhang, F., Ouellet, M., Batth, T. S., Adams, P. D., Petzold, C. J., Mukhopadhyay, A., Keasling, J. D., 2012. Enhancing fatty acid production by the expression of the regulatory transcription factor FadR. Metab. Eng. 14, 653-660. doi:10.1016/j.ymben.2012.08.009

Zhang, L., Tang, Y., Guo, Z., Ding, Z., Shi, G., 2011. Improving the ethanol yield by reducing glycerol formation using cofactor regulation in *Saccharomyces cerevisiae*. Biotechnol. Lett. 33, 1375-80. doi:10.1007/s10529-011-0588-6

Zhou, Y. J., Buijs, N. A., Zhu, Z., Qin, J., Siewers, V., Nielsen, J., 2016. Production of fatty acid-derived oleochemicals and biofuels by synthetic yeast cell factories. Nat. Commun. 7, 11709. doi:10.1038/ncomms11709

Zhu, S., Wu, Y., Chen, Q., Yu, Z., Wang, C., Jin, S., Ding, Y., Wu, G., Tu, S., Xue, Y., 2006. Dissolution of cellulose with ionic liquids and its application: a mini-review. Green Chem. 8, 325. doi:10.1039/b601395c While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

---

What is claimed is:

1. A genetically modified yeast cell comprising the following modifications: a first nucleic acid encoding a *Mus musculus* fatty acid reductase (FAR) (MmFAR1) operatively linked to a promoter, a second nucleic acid encoding acetyl-CoA carboxylase (ACC1) operatively linked to a promoter, a third nucleic acid encoding fatty acid synthase 1 (FAS1) operatively linked to a promoter, and a fourth nucleic acid encoding fatty acid synthase 2 (FAS2) operatively linked to a promoter, wherein the MmFAR1, ACC1, FAS1, and FAS2 have an increased expression compared to expression of each corresponding MmFAR1, ACC1, FAS1, and FAS2 in an unmodified yeast cell, and the genetically modified yeast cell, when grown in 1% yeast extract, 2% peptone, and 2% dextrose (YPD) medium, is capable of producing at least 1.0 g of fatty alcohol per liter of medium.

2. A method of constructing a genetically modified yeast cell comprising: (a) introducing a first nucleic acid encoding *Mus musculus* fatty acid reductase (FAR) MmFAR1 operatively linked to a promoter capable of expressing the MmFAR1 gene product in the yeast cell; (b) introducing a second nucleic acid encoding acetyl-CoA carboxylase (ACC1) operatively linked to a promoter capable of expressing the ACC1 gene product in the yeast cell, or replacing the native promoter of ACC1 with a promoter with a higher transcription activity; (c) introducing a third nucleic acid encoding fatty acid synthase 1 (FAS1) operatively linked to a promoter capable of expressing the FAS1 gene product in the yeast cell, or replacing the native promoter of FAS1 with a promoter with a higher transcription activity; and (d) introducing a fourth nucleic acid encoding fatty acid synthase 2 (FAS2) operatively linked to a promoter capable of expressing the FAS2 gene product in the yeast cell, or replacing the native promoter of FAS2 with a promoter with a higher transcription activity; wherein the higher transcription activity is higher than each corresponding MmFAR1, ACC1, FAS1, and FAS2 in an unmodified yeast cell, and the genetically modified yeast cell, when grown in 1% yeast extract, 2% peptone, and 2% dextrose (YPD) medium, is capable of producing at least 1.0 g of fatty alcohol per liter of medium.

3. A method of producing a fatty alcohol from a genetically modified yeast cell comprising: (a) providing a genetically modified yeast cell of claim 1, and (b) growing or culturing the genetically modified yeast cell in a medium such that the genetically modified yeast cell produces at least 1.0 g of one or more fatty alcohols, or a mixture thereof, per liter of the medium.

4. The genetically modified yeast cell of claim 1; wherein the first nucleic acid encoding MmFAR1 is operatively linked to a GAL1 promoter, or the genetically modified yeast cell further comprises an increased expression of a *Saccharomyces cerevisiae* ACC1 comprising the mutations S659A and S1157A, deleted for a homolog of fatty acid aldehyde (HFD1), deleted for alcohol dehydrogenase (ADH6), deleted for glutamate dehydrogenase (GDH1), deleted for diacylglycerol O-acyltransferase (DGA1), or a nucleic acid encoding a fatty acid-desaturase (OLE1) operatively linked to a promoter.

5. The genetically modified yeast cell of claim 4; wherein the first nucleic acid encoding MmFAR1 is operatively linked to a GAL1 promoter.

6. The genetically modified yeast cell of claim 5 further comprising a nucleic acid encoding a *Saccharomyces cerevisiae* ACC1 comprising the mutations S659A and S1157A operatively linked to a promoter.

7. The genetically modified yeast cell of claim 6 deleted for a homolog of fatty acid aldehyde (HFD1).

8. The genetically modified yeast cell of claim 7 deleted for alcohol dehydrogenase (ADH6).

9. The genetically modified yeast cell of claim 8 deleted for glutamate dehydrogenase (GDH1).

10. The genetically modified yeast cell of claim 9 deleted for diacylglycerol O-acyltransferase (DGA1).

11. The genetically modified yeast cell of claim 10 comprising an increased expression for fatty acid-desaturase (OLE1).

12. The genetically modified yeast cell of claim 4 comprising an increased expression of a *Saccharomyces cerevisiae* ACC1 comprising the mutations S659A and S1157A.

13. The genetically modified yeast cell of claim 4 deleted for a homolog of fatty acid aldehyde (HFD1).

14. The genetically modified yeast cell of claim 4 deleted for alcohol dehydrogenase (ADH6).

15. The genetically modified yeast cell of claim 4 deleted for glutamate dehydrogenase (GDH1).

16. The genetically modified yeast cell of claim 4 deleted for diacylglycerol O-acyltransferase (DGA1).

17. The genetically modified yeast cell of claim 4 comprising a nucleic acid encoding a fatty acid-desaturase (OLE1) operatively linked to a promoter.

18. The genetically modified yeast cell of claim 1, wherein the genetically modified yeast cell, when grown in YPD medium, is capable of producing at least 5.0 g of fatty alcohol per liter of medium.

19. The genetically modified yeast cell of claim 18, wherein the genetically modified yeast cell, when grown in YPD medium, is capable of producing at least 10.0 g of fatty alcohol per liter of medium.

20. The genetically modified yeast cell of claim 1, wherein the genetically modified yeast cell is a *Saccharomyces* cell.

21. The genetically modified yeast cell of claim 20, wherein the *Saccharomyces* cell is a *Saccharomyces cerevisiae* cell.

22. The method of claim 2, wherein the promoter with a higher transcription activity of step (b) is promoter TEF1, the promoter with a higher transcription activity of step (c) is promoter TEF1, and the promoter with a higher transcription activity of step (d) is promoter TEF1.

23. The method of claim 3, wherein the genetically modified yeast cell is a *Saccharomyces* cell.

24. The method of claim 23, wherein the *Saccharomyces* cell is a *Saccharomyces cerevisiae* cell.

25. The method of claim 3, wherein the growing or culturing step is growing or culturing in a continuous culture.

26. The genetically modified yeast cell of claim 1; further comprising a nucleic acid encoding a second MmFAR1 operatively linked to a promoter.

* * * * *

SEQUENCE LISTING

<160> NUMBER OF SEQ ID NOS: 1

<210> SEQ ID NO 1
<211> LENGTH: 515
<212> TYPE: PRT
<213> ORGANISM: Mus musculus

<400> SEQUENCE: 1

```
Met Val Ser Ile Pro Glu Tyr Tyr Glu Gly Lys Asn Ile Leu Leu Thr
1               5                   10                  15

Gly Ala Thr Gly Phe Leu Gly Lys Val Leu Leu Glu Lys Leu Leu Arg
            20                  25                  30

Ser Cys Pro Arg Val Asn Ser Val Tyr Val Leu Val Arg Gln Lys Ala
        35                  40                  45

Gly Gln Thr Pro Gln Glu Arg Val Glu Glu Ile Leu Ser Ser Lys Leu
    50                  55                  60

Phe Asp Arg Leu Arg Asp Glu Asn Pro Asp Phe Arg Glu Lys Ile Ile
65                  70                  75                  80

Ala Ile Asn Ser Glu Leu Thr Gln Pro Lys Leu Ala Leu Ser Glu Glu
                85                  90                  95

Asp Lys Glu Ile Ile Ile Asp Ser Thr Asn Val Ile Phe His Cys Ala
            100                 105                 110

Ala Thr Val Arg Phe Asn Glu Asn Leu Arg Asp Ala Val Gln Leu Asn
        115                 120                 125

Val Ile Ala Thr Arg Gln Leu Ile Leu Leu Ala Gln Gln Met Lys Asn
    130                 135                 140

Leu Glu Val Phe Met His Val Ser Thr Ala Tyr Ala Tyr Cys Asn Arg
145                 150                 155                 160

Lys His Ile Asp Glu Val Val Tyr Pro Pro Val Asp Pro Lys Lys
                165                 170                 175

Leu Ile Asp Ser Leu Glu Trp Met Asp Asp Gly Leu Val Asn Asp Ile
            180                 185                 190

Thr Pro Lys Leu Ile Gly Asp Arg Pro Asn Thr Tyr Ile Tyr Thr Lys
        195                 200                 205

Ala Leu Ala Glu Tyr Val Val Gln Gln Glu Gly Ala Lys Leu Asn Val
```

```
              210                 215                 220
Ala Ile Val Arg Pro Ser Ile Val Gly Ala Ser Trp Lys Glu Pro Phe
225                 230                 235                 240

Pro Gly Trp Ile Asp Asn Phe Asn Gly Pro Ser Gly Leu Phe Ile Ala
                245                 250                 255

Ala Gly Lys Gly Ile Leu Arg Thr Met Arg Ala Ser Asn Asn Ala Leu
                260                 265                 270

Ala Asp Leu Val Pro Val Asp Val Val Val Asn Thr Ser Leu Ala Ala
                275                 280                 285

Ala Trp Tyr Ser Gly Val Asn Arg Pro Arg Asn Ile Met Val Tyr Asn
290                 295                 300

Cys Thr Thr Gly Ser Thr Asn Pro Phe His Trp Gly Glu Val Glu Tyr
305                 310                 315                 320

His Val Ile Ser Thr Phe Lys Arg Asn Pro Leu Glu Gln Ala Phe Arg
                325                 330                 335

Arg Pro Asn Val Asn Leu Thr Ser Asn His Leu Leu Tyr His Tyr Trp
                340                 345                 350

Ile Ala Val Ser His Lys Ala Pro Ala Phe Leu Tyr Asp Ile Tyr Leu
                355                 360                 365

Arg Met Thr Gly Arg Ser Pro Arg Met Met Lys Thr Ile Thr Arg Leu
                370                 375                 380

His Lys Ala Met Val Phe Leu Glu Tyr Phe Thr Ser Asn Ser Trp Val
385                 390                 395                 400

Trp Asn Thr Asp Asn Val Asn Met Leu Met Asn Gln Leu Asn Pro Glu
                405                 410                 415

Asp Lys Lys Thr Phe Asn Ile Asp Val Arg Gln Leu His Trp Ala Glu
                420                 425                 430

Tyr Ile Glu Asn Tyr Cys Met Gly Thr Lys Lys Tyr Val Leu Asn Glu
                435                 440                 445

Glu Met Ser Gly Leu Pro Ala Ala Arg Lys His Leu Asn Lys Leu Arg
                450                 455                 460

Asn Ile Arg Tyr Gly Phe Asn Thr Ile Leu Val Ile Leu Ile Trp Arg
465                 470                 475                 480

Ile Phe Ile Ala Arg Ser Gln Met Ala Arg Asn Ile Trp Tyr Phe Val
                485                 490                 495

Val Ser Leu Cys Tyr Lys Phe Leu Ser Tyr Phe Arg Ala Ser Ser Thr
                500                 505                 510

Met Arg Tyr
            515
```